(12) United States Patent
Abe et al.

(10) Patent No.: US 8,526,696 B2
(45) Date of Patent: *Sep. 3, 2013

(54) MEDICAL IMAGING APPARATUS, MEDICAL IMAGE PROCESSING APPARATUS, ULTRASONIC IMAGING APPARATUS, ULTRASONIC IMAGE PROCESSING APPARATUS AND METHOD OF PROCESSING MEDICAL IMAGES

(75) Inventors: Yasuhiko Abe, Otawara (JP); Tetsuya Kawagishi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 752 days.

This patent is subject to a terminal disclaimer.

(21) Appl. No.: 12/693,773

(22) Filed: Jan. 26, 2010

(65) Prior Publication Data

US 2010/0195887 A1     Aug. 5, 2010

(30) Foreign Application Priority Data

Feb. 5, 2009 (JP) .................................. 2009-024643

(51) Int. Cl.
*G06K 9/00* (2006.01)
(52) U.S. Cl.
USPC ........................................................ 382/131

(58) Field of Classification Search
None
See application file for complete search history.

(56) References Cited

U.S. PATENT DOCUMENTS

| 2001/0032649 | A1* | 10/2001 | Nagano | 128/897 |
|---|---|---|---|---|
| 2002/0188174 | A1* | 12/2002 | Aizawa et al. | 600/118 |
| 2003/0083578 | A1* | 5/2003 | Abe et al. | 600/447 |
| 2009/0270732 | A1 | 10/2009 | Abe et al. | |

FOREIGN PATENT DOCUMENTS

| JP | 2003-175041 | 6/2003 |
|---|---|---|
| JP | 2003-250804 | 9/2003 |
| JP | 2009-261638 | 11/2009 |

* cited by examiner

*Primary Examiner* — Valerie Lubin
(74) *Attorney, Agent, or Firm* — Oblon, Spivak, McClelland, Maier & Neustadt, L.L.P.

(57) ABSTRACT

Based on medical image data acquired in each time phase included in a one-cycle interval, first tracking part tracks the position of a first region of interest set in a first time phase in each time phase and tracks the position of a second region of interest set in a second time phase in each time phase. Based on position information of the first region of interest and the second region of interest in each time phase, position correction part obtains position information of a region of interest in each time phase so that it passes through the position of the first region of interest in the first time phase and the position of the second region of interest in the second time phase. Motion-information calculator obtains motion information of a tissue based on the obtained position information.

23 Claims, 12 Drawing Sheets

MEDICAL IMAGING APPARATUS, MEDICAL IMAGE PROCESSING APPARATUS, ULTRASONIC IMAGING APPARATUS, ULTRASONIC IMAGE PROCESSING APPARATUS AND METHOD OF PROCESSING MEDICAL IMAGES

BACKGROUND OF THE INVENTION

1. Field of the Invention

This invention relates to a medical imaging apparatus and an ultrasonic imaging apparatus that acquire medical images representing a subject and uses those medical images to obtain the state of motion of the subject. The invention also relates to both a medical image processing apparatus and an ultrasonic image processing apparatus that obtain the state of motion of a subject by using medical images as well as a method of processing medical images.

2. Description of the Related Art

Objective and quantitative functional evaluations of living tissue such as the myocardium are extremely important for diagnosing the living tissue. For example, methods for acquiring image data of a heart using an ultrasonic imaging apparatus to conduct quantitative evaluations based on the image data have been proposed.

As one example, technology (hereinafter referred to as "speckle tracking", or "ST") for calculating local wall-motion information including myocardial displacement and deformation while performing tracking of two-dimensional and three-dimensional ultrasonic images by using a local pattern-matching process has been put into practical use according to Japanese published unexamined application 2003-175041 and Japanese published unexamined application 2003-250804.

In the ST method, generally, the endocardial contour and the epicardial contour of the myocardium are defined as the initial tracking positions during the end diastole (the cardiac phase at which the first R wave is detected) or the end systole. Then, in the remaining cardiac phases, by automatically tracking the initial tracking position by using motion vector information acquired through a local pattern-matching process, the endocardial contour and the epicardial contour are tracked in all required time phases.

In the tracking process based on the ST method, it is difficult to estimate the motion vector during diastole (especially early diastole phase E'), when the movement speed of the heart is fastest, and tracking of the contours in cardiac phase E' deviates easily. Therefore, the applicants of the present application proposed a means of automatically updating the tracking results after cardiac phase E' onward by manually correcting the contour position to perform retracking in the forward direction when the tracking of the contour deviates after the cardiac phase E' (Patent Application 2008-114854).

Here, the retracking method proposed in Patent Application 2008-114854 may be referred to as the "ReTrack2" function.

However, tracking errors may occur not only during diastole but also during systole (cardiac phase S', in which the motion is relatively slow). Sequential corrections of tracking errors occurring during systole or diastole using only the above tracking method (ReTrack2 function) in order to obtain more accurate evaluation results are troublesome and inconvenient.

SUMMARY OF THE INVENTION

The purpose of this invention is to provide a medical imaging apparatus, a medical image processing apparatus, an ultrasonic imaging apparatus, an ultrasonic image processing apparatus and a method of processing medical images in which, during processes of tracking a region of interest, deviations from the tracking position are unlikely to occur from when tracking is started, and even when there is a deviation in the tracking position, the tissue movement included in the region of interest may be evaluated more accurately by correcting the tracking position through simple operations.

A first aspect of this invention is a medical imaging apparatus comprising: an imaging part configured to capture a cyclically moving subject in order to acquire a plurality of medical image data representing said subject over a single cycle or more; a ROI setting part configured to set a first region of interest of a tissue represented in medical image data acquired in a first time phase included in a one-cycle interval and to set a second region of interest of said tissue represented in medical image data acquired in a second time phase differing from said first time phase included in said one-cycle interval; a tracking part configured to track in each time phase the position corresponding to said first region of interest in said one-cycle interval including the remaining time phases based on medical image data acquired in each time phase included in said one-cycle interval, and configured to track in each time phase the position corresponding to said second region of interest in said one-cycle interval including the remaining time phases based on the medical image data acquired in said each time phase; a position correction part configured to obtain position information of a region of interest of said tissue in said each time phase, based on position information of said first region of interest and said second region of interest in said each time phase acquired by said tracking part, so that it passes through both the position of said first region of interest set in said first time phase and the position of said second region of interest set in said second time phase; a motion-information calculator configured to obtain motion information of said tissue based on said obtained position information of a region of interest in said each time phase; and a display controller configured to cause a display to display said motion information.

According to this first aspect, based on the position information of the first region of interest and the second region of interest in each time phase, position information of a region of interest that is of the tissue in each time phase is obtained in order to pass through the position of the first region of interest set in the first time phase and the position of the second region of interest set in the second time phase.

This allows deviations in the tracking performed by the tracking part to become less likely. Moreover, even if there is a deviation in the tracking performed by the tracking part, the movement of the tissue may be obtained more accurately by correcting the tracking position through a simple operation.

Moreover, a second aspect of this invention is medical imaging apparatus comprising: an imaging part configured to capture a cyclically moving subject to acquire a plurality of medical image data representing said subject over a single cycle or more; a first-ROI setting part configured to set a first region of interest of a tissue represented by medical image data acquired in a first time phase during systole included in a one-cycle interval; a first tracking part configured to track in each time phase the position corresponding to said first region of interest in said one-cycle interval including the remaining time phases, based on medical image data acquired in each time phase included in said one-cycle interval; a second-ROI setting part configured to correct the position of said tracked first region of interest in a second time phase differing from said first time phase during systole included in said one-cycle interval after said tracking performed by said first tracking part, in order to set a second region of interest of said tissue in said second time phase; a second tracking part configured to track in each time phase the position corresponding to said second region of interest in an interval including the interval between said first time phase and said second time phase, based on medical image data acquired in said each time phase; a position correction part configured to obtain position information of a region of interest of said tissue in said each time phase, based on position information of said first region of interest and said second region of interest in said each time phase acquired by said first tracking part and said second tracking part respectively, so that it passes through both the position of said first region of interest in said first time phase and the position of said second region of interest in said second time phase; a motion-information calculator configured to obtain motion information of said tissue based on said obtained position information of a region of interest in said each time phase; and a display controller configured to cause a display to display said motion information.

Moreover, a third aspect of this invention is a medical image processing apparatus comprising: a storage configured to store a plurality of medical image data that represents a cyclically moving subject by capturing the subject over a single cycle or more; a ROI setting part configured to set a first region of interest of a tissue represented in medical image data acquired in a first time phase included in a one-cycle interval and to set a second region of interest of said tissue represented in medical image data acquired in a second time phase differing from said first time phase included in said one-cycle interval; a tracking part configured to track in each time phase the position corresponding to said first region of interest in said one-cycle interval including the remaining time phases, based on medical image data acquired in each time phase included in said one-cycle interval and configured to track in each time phase the position corresponding to said second region of interest in said one-cycle interval including the remaining time phases, based on the medical image data acquired in said each time phase; a position correction part configured to obtain position information of a region of interest of said tissue in said each time phase, based on position information of said first region of interest and said second region of interest in said each time phase acquired by said tracking part, so that it passes through the position of said first region of interest set in said first time phase and the position of said second region of interest set in said second time phase; a motion-information calculator configured to obtain motion information of said tissue based on said obtained position information of a region of interest in said each time phase; and a display controller configured to cause a display to display said motion information.

Moreover, a fourth aspect of this invention is a medical image processing apparatus comprising: a storage configured to store a plurality of medical image data that represents a cyclically moving subject acquired by capturing the subject over a single cycle or more; a first-ROI setting part configured to set a first region of interest of a tissue represented by medical image data acquired in a first time phase during systole included in a one-cycle interval; a first tracking part configured to track in each time phase the position corresponding to said first region of interest in said one-cycle interval including the remaining time phases, based on medical image data acquired in each time phase included in said one-cycle interval; a second-ROI setting part configured to correct the position of said tracked first region of interest in a second time phase differing from said first time phase during systole included in said one-cycle interval after said tracking performed by said first tracking part, to set a second region of interest of said tissue in said second time phase; a second tracking part configured to track in each time phase the position corresponding to said second region of interest in an interval including the interval between said first time phase and said second time phase, based on medical image data acquired in said each time phase; a position correction part configured to obtain position information of a region of interest of said tissue in said each time phase, based on position information of said first region of interest and said second region of interest in said each time phase acquired by said first tracking part and said second tracking part respectively, so that it passes through both the position of said first region of interest in said first time phase and the position of said second region of interest in said second time phase; a motion-information calculator configured to obtain motion information of said tissue based on said obtained position information of a region of interest in said each time phase; and a display controller configured to cause a display to display said motion information.

Moreover, a fifth aspect of this invention is a medical imaging apparatus comprising: an imaging part configured to capture a heart of a subject by means of ultrasound in order to acquire a plurality of ultrasonic image data representing said heart over a single cycle or more; a ROI setting part configured to set a first region of interest of a tissue represented in ultrasonic image data acquired in a first time phase included in a one-cycle interval and to set a second region of interest of said tissue represented in ultrasonic image data acquired in a second time phase differing from said first time phase included in said one-cycle interval; a tracking part configured to track in each time phase the position corresponding to said first region of interest in said one-cycle interval including the remaining time phases based on ultrasonic image data acquired in each time phase included in said one-cycle interval, and configured to track in each time phase the position corresponding to said second region of interest in said one-cycle interval including the remaining time phases based on the ultrasonic image data acquired in said each time phase; a position correction part configured to obtain position information of a region of interest of said tissue in said each time phase, based on position information of said first region of interest and said second region of interest in said each time phase acquired by said first tracking part and said second tracking part respectively, so that it passes through both the position of said first region of interest set in said first time phase and the position of said second region of interest set in said second time phase; a motion-information calculator configured to obtain motion information of said tissue based on said obtained position information of a region of interest in said each time phase; and a display controller configured to cause a display to display said motion information.

Moreover, a sixth aspect of this invention is a medical imaging apparatus comprising: an imaging part configured to capture a heart of a subject by means of ultrasound to acquire a plurality of ultrasonic image data representing said heart over a single cycle or more; a first-ROI setting part configured to set a first region of interest of a tissue represented by ultrasonic image data acquired in a first time phase during systole included in a one-cycle interval; a first tracking part configured to track in each time phase the position corresponding to said first region of interest in said one-cycle interval including the remaining time phases, based on ultrasonic image data acquired in each time phase included in said one-cycle interval; a second-ROI setting part configured to correct the position of said tracked first region of interest in a second time phase differing from said first time phase during systole included in said one-cycle interval after said tracking performed by said first tracking part, in order to set a second region of interest of said tissue in said second time phase; a second tracking part configured to track in each time phase the position corresponding to said second region of interest in an interval including the interval between said first time phase and said second time phase, based on ultrasonic image data acquired in said each time phase; a position correction part configured to obtain position information of a region of interest of said tissue in said each time phase, based on position information of said first region of interest and said second region of interest in said each time phase acquired by said first tracking part and said second tracking part respectively, so that it passes through both the position of said first region of interest in said first time phase and the position of said second region of interest in said second time phase; a motion-information calculator configured to obtain motion information of said tissue based on said obtained position information of a region of interest in said each time phase; and a display controller configured to cause a display to display said motion information.

Moreover, a seventh aspect of this invention is a medical image processing apparatus comprising: a storage configured to store a plurality of ultrasonic image data that represents a heart of a subject acquired over a single cycle or more by capturing the subject by means of ultrasound; a ROI setting part configured to set a first region of interest of a tissue represented in ultrasonic image data acquired in a first time phase included in a one-cycle interval and to set a second region of interest of said tissue represented in ultrasonic image data acquired in a second time phase differing from said first time phase included in said one-cycle interval; a tracking part configured to track in each time phase the position corresponding to said first region of interest in said one-cycle interval including the remaining time phases, based on ultrasonic image data acquired in each time phase included in said one-cycle interval and configured to track in each time phase the position corresponding to said second region of interest in said one-cycle interval including the remaining time phases, based on the ultrasonic image data acquired in said each time phase; a position correction part configured to obtain position information of a region of interest of said tissue in said each time phase, based on position information of said first region of interest and said second region of interest in said each time phase acquired by said tracking part, so that it passes through the position of said first region of interest set in said first time phase and the position of said second region of interest set in said second time phase; a motion-information calculator configured to obtain motion information of said tissue based on said obtained position information of a region of interest in said each time phase; and a display controller configured to cause a display to display said motion information.

Moreover, a eighth aspect of this invention is a medical image processing apparatus comprising: a storage configured to store a plurality of ultrasonic image data that represents a heart of a subject acquired over a single cycle or more by capturing the subject by means of ultrasound; a first-ROI setting part configured to set a first region of interest of a tissue represented by ultrasonic image data acquired in a first time phase during systole included in a one-cycle interval; a first tracking part configured to track in each time phase the position corresponding to said first region of interest in said one-cycle interval including the remaining time phases, based on ultrasonic image data acquired in each time phase included in said one-cycle interval; a second-ROI setting part configured to correct the position of said tracked first region of interest in a second time phase differing from said first time phase during systole included in said one-cycle interval after said tracking performed by said first tracking part, to set a second region of interest of said tissue in said second time phase; a second tracking part configured to track in each time phase the position corresponding to said second region of interest in an interval including the interval between said first time phase and said second time phase, based on ultrasonic image data acquired in said each time phase; a position correction part configured to obtain position information of a region of interest of said tissue in said each time phase, based on position information of said first region of interest and said second region of interest in said each time phase acquired by said first tracking part and said second tracking part respectively, so that it passes through both the position of said first region of interest in said first time phase and the position of said second region of interest in said second time phase; a motion-information calculator configured to obtain motion information of said tissue based on said obtained position information of a region of interest in said each time phase; and a display controller configured to cause a display to display said motion information.

Moreover, a ninth aspect of this invention is a method of processing medical images, comprising: capturing a cyclically moving subject to acquire a plurality of medical image data representing said subject over a single cycle or more; setting a first region of interest of a tissue represented in medical image data acquired in a first time phase included in a one-cycle interval and setting a second region of interest of said tissue represented in medical image data acquired in a second time phase differing from said first time phase included in said one-cycle interval; tracking in each time phase the position corresponding to said first region of interest in said one-cycle interval including the remaining time phases, based on medical image data acquired in each time phase included in said one-cycle interval, and tracking in each time phase the position corresponding to said second region of interest in said one-cycle interval including the remaining time phases, based on medical image data acquired in said each time phase; obtaining position information of a region of interest of said tissue in said each time phase, based on position information of said first region of interest and said second region of interest in said each time phase acquired by said first tracking part and said second tracking part, respectively, so that it passes through both the position of said first region of interest set in said first time phase and the position of said second region of interest set in said second time phase; obtaining motion information of said tissue based on said obtained position information of a region of interest in said each time phase; and displaying said motion information.

Moreover, a tenth aspect of this invention is a method of processing medical images, comprising: a method of processing medical images, comprising: capturing a cyclically moving subject to acquire a plurality of medical image data representing said subject over a single cycle or more; setting a first region of interest of a tissue represented by medical image data acquired in a first time phase during systole included in a one-cycle interval; tracking in each time phase the position corresponding to said first region of interest in said one-cycle interval including the remaining time phases, based on medical image data acquired in each time phase included in said one-cycle interval; correcting the position of said tracked first region of interest in a second time phase differing from said first time phase during systole included in said one-cycle interval after said tracking performed by said first tracking part, to set a second region of interest of said tissue in said second time phase; tracking in each time phase the position corresponding to said second region of interest in an interval including the interval between said first time phase and said second time phase, based on medical image data acquired in said each time phase; obtaining position information of a region of interest of said tissue in said each time phase, based on position information of said first region of interest and said second region of interest in said each time phase acquired by said first tracking part and said second tracking part, respectively, so that it passes through both the position of said first region of interest in said first time phase and the position of said second region of interest in said second time phase; obtaining motion information of said tissue based on said obtained position information of a region of interest in said each time phase; and displaying said motion information.

DETAILED DESCRIPTION OF THE EMBODIMENTS

First Illustrative Embodiment

Figure 1:
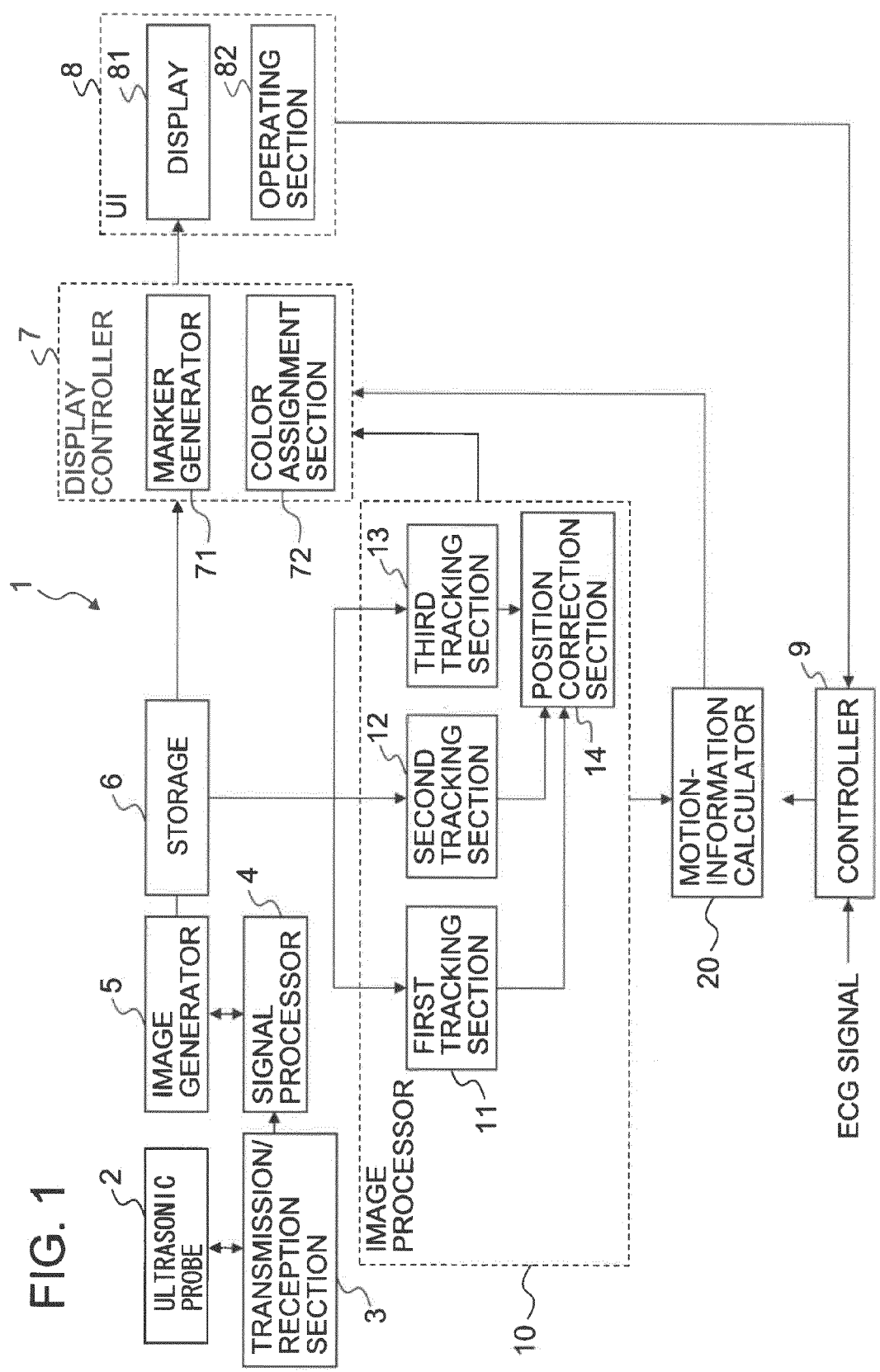
FIG. 1 is a block diagram showing an ultrasonic imaging apparatus related to an illustrative embodiment of this invention.

An ultrasonic imaging apparatus, an MRI (Magnetic Resonance Imaging) device, or an X-ray CT (X-ray Computed Tomography) device may be used as a medical imaging apparatus related to an illustrative embodiment of this invention. As an example of a medical imaging apparatus, an ultrasonic imaging apparatus will be described. An ultrasonic imaging apparatus related to an embodiment of this invention will be described with reference to FIG. 1.

An ultrasonic imaging apparatus 1 comprises: an ultrasonic probe 2; a transmission/reception section 3; a signal processor 4; an image generator 5; a storage 6; a display controller 7; a user interface (UI) 8; a controller 9; an image processor 10; and a motion-information calculator 20. Moreover, the storage 6, the display controller 7, the user interface (UI) 8, the image processor 10, and the motion-information calculator 20 may be used to compose a medical image processing apparatus.

For the ultrasonic probe 2, either a 1D array probe, in which a plurality of ultrasonic transducers are arranged in a single row in a predetermined direction (scanning direction), or a 2D array probe, in which a plurality of ultrasonic transducers are arranged two-dimensionally, is used. Moreover, a 1D array probe in which ultrasonic transducers are arranged in a predetermined direction (scanning direction) and may be mechanically rotated to a direction (rotated direction) perpendicular to the scanning direction may be used.

The transmission/reception section 3 comprises a transmitter and a receiver and causes the ultrasonic probe 2 to generate ultrasonic waves by providing electrical signals thereto and receives echo signals received by the ultrasonic probe 2.

The transmitter of the transmission/reception section 3 comprises a clock generation circuit, a transmission delay circuit, and a pulsar circuit that are not shown in the diagram. The clock generation circuit generates clock signals that determine the transmission timing and transmission frequency of the ultrasonic wave signals. The transmission delay circuit conducts transmission focuses by applying a delay during transmission of the ultrasonic waves. The pulsar circuit includes the same number of pulsars as individual channels corresponding to each ultrasonic transducer and generates a drive pulse at the delayed transmission timing to provide electrical signals to each ultrasonic transducer of the ultrasonic probe 2.

The receiver of the transmission/reception section 3 comprises a preamplifier circuit, an A/D conversion circuit, a reception delay circuit, and an adding circuit. The preamplifier circuit amplifies echo signals output from each ultrasonic transducer of the ultrasonic probe 2 for each reception channel. The A/D conversion circuit performs A/D conversion of the amplified echo signals. The reception delay circuit provides the delay time necessary to determine the reception directivity of the A/D-converted echo signals. The adding circuit adds the delayed echo signals. Based on this addition, reflection components from the direction corresponding to the reception directivity are emphasized. These signals that undergo the addition process of the transmission/reception section 3 may be abbreviated as "RF data (raw data)". The transmission/reception section 3 outputs the RF data to the signal processor 4.

The ultrasonic probe 2 and the transmission/reception section 3 constitute one example of an "imaging part" of this invention.

The signal processor 4 comprises a B-mode processor, a CFM (Color Flow Mapping) processor, and the like. The B-mode processor performs image conversion of the echo amplitude information.

Specifically, the B-mode processor performs a Band Pass Filter process for the received signals output from the transmission/reception section 3 before detecting the envelope curve of the output signals.

Then, the B-mode processor performs image conversion of the echo amplitude information by implementing a compression process for the detected data through a logarithmic conversion. Moreover, the CFM processor performs image conversion of the moving blood flow information. The blood flow information includes information such as velocity, dispersion, and power and is acquired as binarized information.

The image generator 5 converts (digital scan conversion) the signal-processed data into coordinate system data based on spatial coordinates. For example, the image generator 5 generates B-mode image data (hereinafter also referred to as "cross-sectional image data") representing the tissue form of the subject by implementing a scan conversion process of the signal-processed data output from the B-mode processor. Then, the image generator 5 outputs the cross-sectional image data and other ultrasonic image data to the storage 6.

Moreover, when a volume scan is performed by the ultrasonic probe 2 and the transmission/reception section 3, the image generator 5 may receive volume data from the signal processor 4 and generate three-dimensional image data representing the tissue in three dimensions by implementing volume rendering of the volume data.

Furthermore, the image generator 5 may generate image data (MPR image data) of an arbitrary cross section by implementing an MPR (Multi-Planar Reconstruction) process of the volume data. Then, the image generator 5 outputs ultrasonic image data such as the three-dimensional image data and MPR image data to the storage 6.

Ultrasonic image data such as the cross-sectional image data and three-dimensional image data generated by the image generator 5 is stored in the storage 6. Moreover, when electrocardiogram signals of the subject have been acquired, the controller 9 receives the electrocardiogram signals from outside the ultrasonic imaging apparatus 1 and stores the ultrasonic image data in the storage 6 in connection with the cardiac phase received at the timing at which the ultrasonic image data was generated. The ultrasonic image data corresponds to one example of the "medical image data" of this invention.

The ultrasonic imaging apparatus 1 related to the first illustrative embodiment acquires cross-sectional image data representing the heart of a subject in each cardiac phase by ultrasonically scanning the heart. In other words, the ultrasonic imaging apparatus 1 acquires moving image data representing the heart.

For example, the ultrasonic imaging apparatus 1 acquires a plurality of cross-sectional image data (moving image data) representing the heart of a subject over one cardiac cycle or more by ultrasonically scanning the heart over one cardiac cycle or more.

Moreover, when electrocardiogram signals have been acquired, the controller 9 stores in the storage 6 each item of cross-sectional image data in connection with the cardiac phase received at the timing at which the cross-sectional image data was generated. Consequently, each of a plurality of cross-sectional image data is stored in the storage 6 in connection with the cardiac phase in which the cross-sectional image data was generated.

The display controller 7 reads the cross-sectional image data from the storage 6 and causes the display 81 to display cross-sectional images based on the cross-sectional image data. For example, when an operator specifies an arbitrary cardiac phase by using the operating section 82, information indicating the specified cardiac phase is output from the user interface (UI) 8 to the display controller 7. The display controller 7 reads the cross-sectional image data in connection with the specified cardiac phase from the storage 6 and causes the display 81 to display a cross-sectional image based on the cross-sectional image data.

(Image Processor 10)

The image processor 10 comprises a first tracking section 11, a second tracking section 12, a third tracking section 13, and a position correction section 14.

The image processor 10 defines, as initial contours, the contour (region of interest) of a specific tissue specified on cross-sectional images representing the heart and performs pattern matching between two cross-sectional images acquired in different cardiac phases, in order to obtain the position of the contour in each cardiac phase.

In this illustrative embodiment, as an example, the image processor 10 performs pattern matching for contours specified in two cardiac phases by defining the contours as the initial contours in their respective cardiac phases and also corrects the contour position in each cardiac phase so that the position passes through the two initial contour positions.

For example, when a first initial contour position IC1 is specified during the end diastole ED and a second initial contour position IC2 is specified during the end systole ES, the image processor 10 obtains the contour position in each cardiac phase by using the first initial contour position IC1 and also obtains the contour position in each cardiac phase by using the second initial contour position IC2. Then, the image processor 10 obtains the contour position in each cardiac phase so that the position passes through the first initial contour position IC1 during the end diastole ED and through the second initial contour position IC2 during the end systole ES.

Here, the method of specifying the above initial contour (region of interest) will be described. In this illustrative embodiment, a case will be described in which the endocardial contour and the epicardial contour of the heart are specified.

First, the operator specifies an arbitrary cardiac phase using the operating section 82. The display controller 7 reads the cross-sectional image data acquired in the cardiac phase specified by the operator from the storage 6 and causes the display 81 to display a cross-sectional image based on the cross-sectional image data. In this illustrative embodiment, because cross-sectional image data representing the heart is acquired, a cross-sectional image representing the heart is displayed on the display 81. For example, by scanning a cross section (hereinafter, "longitudinal cross section") along the longitudinal direction of the heart using the ultrasonic probe 2 and the transmission/reception section 3, cross-sectional image data (hereinafter "longitudinal image data") of the longitudinal cross section is acquired. Then, the display controller 7 causes the display 81 to display a longitudinal image based on the longitudinal image data acquired in the cardiac phase specified by the operator.

For example, when the end diastole ED is specified by the operator, the display controller 7 reads the cross-sectional image data acquired during the end diastole ED from the storage 6 and causes the display 81 to display a cross-sectional image based on the cross-sectional image data.

Alternatively, when the end systole ES is specified by the operator, the display controller 7 reads the cross-sectional image data acquired during the end systole ES from the storage 6 and causes the display 81 to display the cross-sectional image data.

The cross-sectional image data is stored in the storage 6 in connection with the cardiac phase in which the cross-sectional image data was acquired. Therefore, the display controller 7 reads the cross-sectional image data acquired in cardiac phases such as the end diastole ED and the end systole ES from the storage 6 and causes the display 81 to display cross-sectional images based on the cross-sectional image data of each cardiac phase.

Then, by using the operating section 82 to trace over the two-dimensional contour of the endocardium shown in the cross-sectional image, the operator specifies the two-dimensional contour of the endocardium in the cross-sectional image. When the two-dimensional contour of the endocardium is specified in this way, coordinate information indicating the position of the two-dimensional contour of the endocardium is output from the user interface (UI) 8 to the image processor 10 through the controller 9.

Furthermore, by using the operating section 82 to trace over the two-dimensional contour of the epicardium shown in the cross-sectional image, the operator specifies the two-dimensional contour of the epicardium in the cross-sectional image. When the two-dimensional contour of the epicardium is specified in this way, coordinate information indicating the position of the two-dimensional contour of the epicardium is output from the user interface (UI) 8 to the image processor 10 through the controller 9.

(First Tracking Section 11)

In the image processor 10, the first tracking section 11 receives coordinate information of the endocardial contour and coordinate information of the epicardial contour from the user interface (UI) 8. A specified two-dimensional contour of an endocardium is set as the initial contour of the endocardium in the first tracking section 11.

Moreover, a specified two-dimensional contour of an epicardium is set as the initial contour of the epicardium in the first tracking section 11. For example, the two-dimensional contour of the endocardium during end diastole ED is set as the initial contour of the endocardium. Moreover, the two-dimensional contour of the epicardium during end diastole ED is set as the initial contour of the epicardium.

As described above, when a two-dimensional contour of the endocardium (initial endocardial contour) during an arbitrary cardiac phase is specified by the operator, the first tracking section 11 performs pattern matching (ST processing) using the speckle pattern for two items of cross-sectional image data acquired at different times.

In this pattern matching process, the first tracking section 11 obtains the position of each point composing the two-dimensional contour of the endocardium for each item of cross-sectional image data acquired during each cardiac phase. Then, the first tracking section 11 obtains the position of each point on the two-dimensional contour of the endocardium in each item of cross-sectional image data generated during each cardiac phase. In this way, the first tracking section 11 tracks each point composing the two-dimensional contour of the endocardium over time.

For example, the first tracking section 11 receives the coordinate information of each point composing the endocardial contour set as the initial contour and reads the cross-sectional image data (hereinafter also referred to as "cross-sectional image data 13") generated in the cardiac phase following that of the cross-sectional image data (hereinafter also referred to as "cross-sectional image data A") in which the initial contour was set from the storage 6. Then, the first tracking section 11 performs pattern matching using the speckle pattern for two timely consecutive cross-sectional images to obtain the motion vector of each point composing the endocardial contour.

Specifically, the first tracking section 11 obtains the motion vector of each point composing the endocardial contour by performing pattern matching using the speckle pattern for cross-sectional image A and cross-sectional image B. This motion vector represents the displacement of each point composing the contour and the direction of movement in which each point has been displaced. In other words, the first tracking section 11 perform pattern matching for two cross-sectional images and calculates the amount of movement of the speckles to obtain the motion vector of each point composing the contour. By obtaining the motion vector of each point composing the contour in this way, the position of each point composing the endocardial contour during the cardiac phase in which the cross-sectional image data B was generated is obtained.

Furthermore, the first tracking section 11 reads the cross-sectional image data (hereinafter also referred to as "cross-sectional image data C") generated in the cardiac phase following that of the cross-sectional image data B from the storage 6.

Then, the first tracking section 11 obtains the motion vector of each point composing the endocardial contour by performing pattern matching using the speckle pattern for the two timely consecutive cross-sectional images (cross-sectional image B and cross-sectional image C). In this way, the position of each point composing the endocardial contour during the cardiac phase in which the cross-sectional image data C was generated is obtained.

In the manner described above, the first tracking section 11 performs pattern matching (ST processing) using the speckle pattern to obtain the motion vector of each point composing the endocardial contour for each cardiac phase in which each item of cross-sectional image data was generated. In this way, the first tracking section 11 tracks the motion vector at each point composing the endocardial contour over time. As a result, it becomes possible to track each point composing the two-dimensional contour of the endocardium over time.

For example, the first tracking section 11 obtains the position of each point composing the two-dimensional contour of the endocardium in each cardiac phase in all items of cross-sectional image data acquired over one cardiac cycle. In this way, the position of each point composing the two-dimensional contour of the endocardium in each cardiac phase over one cardiac cycle is obtained.

Moreover, when the two-dimensional contour of the epicardium (initial epicardial contour) is set, as with the tracking of the endocardium, the first tracking section 11 performs pattern matching using the speckle pattern for two images. Through this pattern matching process, the first tracking section 11 obtains the position of each point composing the two-dimensional contour of the epicardium for each item of cross-sectional image data generated in each cardiac phase. In this way, the first tracking section 11 tracks each point composing the two-dimensional contour of the epicardium over time.

Furthermore, the first tracking section 11 may obtain the normal vector at each specified position on the endocardium and define positions located at a fixed distance outside from each position on the endocardium in the direction of the normal vector as the two-dimensional contour of the epicardium. For example, the first tracking section 11 defines positions located 8 mm outside from the positions of the endocardium as the epicardial contour. This fixed distance may be changed to an arbitrary value by the operator. The two-dimensional contour of the epicardium defined here is set in the first tracking section 11 as the initial epicardial contour to be tracked.

Then, the first tracking section 11 tracks each position composing the two-dimensional contour of the epicardium over time.

Then, the first tracking section 11 outputs the coordinate information of each point composing the two-dimensional contour of the endocardium and the coordinate information of each point composing the two-dimensional contour of the epicardium during each cardiac phase to the position correction section 14. The first tracking section 11 is one example of a "tracking part" and a "first tracking part" of this invention.

A specified example of the first illustrative embodiment will now be described. As an example, one heartbeat (one cardiac cycle) (cardiac phase t=end diastole $ED_0$ to end diastole $ED_1$) is defined as the tracking period. A case in which initial contours are set for both the end diastole ED and the end systole ES to perform a tracking process will be described.

(Step S01)

First, using the operating section 82, the operator specifies one heartbeat (cardiac phase t=end diastole $ED_0$ to the following end diastole $ED_1$). When the one heartbeat is set, information indicating the specified cardiac phase (end diastole $ED_0$ to the following end diastole $ED_1$) is output from the user interface (UI) 8 to the image processor 10 and the display controller 7.

(Step S02)

Next, using the operating section 82, the operator specifies the position of a first initial contour in a first initial time phase.

Specifically, the display controller 7 reads the cross-sectional data in the first initial time phase from the storage 6 and causes the display 81 to display a cross-sectional image based on the cross-sectional image data. For example, when the operator specifies the end diastole $ED_0$ as the first initial time phase $T_1$ by using the operating section 82, the display controller 7 causes the display 81 to display the cross-sectional image in the end diastole $ED_0$. Then, using the operating section 82, the operator specifies a first initial contour position IC1 of the endocardium on the cross-sectional image in the end diastole $ED_0$.

(Step S03)

Furthermore, using the operating section 82, the operator specifies a position of a second initial contour in a second initial time phase differing from the first initial time phase. For example, when the operator specifies the end systole ES as the second initial time phase $T_2$ by using the operating section 82, the display controller 7 causes the display 81 to display the cross-sectional image in the end systole ES. Then, using the operating section 82, the operator specifies the first initial contour position IC1 of the endocardium on the cross-sectional image in the end systole ES.

(Step S04)

The first tracking section 11 defines the operator-specified first initial contour position IC1 as the tracking subject. Then, the first tracking section 11 performs ST processing for cross-sectional image data in each cardiac phase acquired in one heartbeat (end diastole $ED_0$ to the following end diastole $ED_1$) to obtain the endocardial contour position $P_0(t)$ in each cardiac phase within one heartbeat including the remaining cardiac phases.

Moreover, the first tracking section 11 defines the operator-specified second initial contour position IC2 as a separate tracking subject. Then, the first tracking section 11 performs ST processing for cross-sectional image data in each cardiac phase acquired in one heartbeat (end diastole $ED_0$ to the following end diastole $ED_1$) to obtain the endocardial contour position $P_1(t)$ in each cardiac phase within one heartbeat including the remaining cardiac phases.

Then, based on the endocardial contour position $P_0(t)$ in each cardiac phase and the endocardial contour position $P_1(t)$ in each cardiac phase, the position correction section 14 obtains the endocardial contour position P(t) in each cardiac phase that passes through the first initial contour position IC1 during the end diastole $ED_0$ and through the second initial contour position IC2 during the end systole ES.

The contour position $P_0(t)$ is the endocardial contour position acquired by using the first initial contour position IC1 as the tracking subject. Moreover, the contour position $P_1(t)$ is the endocardial contour position acquired by using the second initial contour position IC2 as the tracking subject.

The position correction section 14 is one example of a "position correction part" of this invention.

The position correction section 14 obtains the contour position P (t) through the first method or the second method described below.

(First Method)

For example, the position correction section 14 obtains the contour position P(t) in each cardiac phase included in one heartbeat by connecting the contour position $P_0(t)$ acquired based on the first initial contour position IC1 and the contour position $P_1(t)$ acquired based on the second initial contour position IC2 in a cardiac phase tm between the end diastole $ED_0$ and the end systole ES.

The cardiac phase tm is preferably a medial time (ES−$ED_0$)/2) between the end diastole $ED_0$ and the end systole ES. Moreover, the cardiac phase tm may be a time other than the medial time.

Furthermore, in cardiac phase tm, it is assumed that there will be displacement between the contour position $P_0(t)$ and the contour position $P_1(t)$. Consequently, after the contour positions are connected, the position correction section 14 performs a contour-position smoothing process and a contour-position fitting process in the temporal direction near the cardiac phase tm so that the two contour positions connect smoothly over time near the cardiac phase tm.

(Second Method)

The position correction section 14 may obtain the contour position P(t) in each cardiac phase within one heartbeat by performing weighting according to time for the contour position $P_0(t)$ acquired based on the first initial contour position IC1 and the contour position $P_1(t)$ acquired based on the second initial contour position IC2 and adding the positions.

For example, for the contour position $P_0(t)$, a first weighting function $W_0(t)$ is applied. The first weighting function $W_0(t)$ is a weighting function in which the weighting becomes "1" in the end diastole $ED_0$ and gradually decreases as time progresses from the end diastole $ED_0$ to the end systole ES to become "0" in the end systole ES.

Moreover, in the first weighting function $W_0(t)$, the weighting gradually increases as time progresses from the end systole ES to the following end diastole $ED_1$ and becomes "1" in the end diastole $ED_1$.

For the contour position $P_1(t)$, a second weighting function $W_1(t)$ is applied. The second weighting function $W_1(t)$ is a weighting function in which the weighting becomes "0" in the end diastole $ED_0$ and gradually increases as time progresses from the end diastole $ED_0$ to the end systole ES to become "1" in the end systole ES. Moreover, in the second weighting function $W_1(t)$, the weighting gradually decreases as time progresses from the end systole ES to the following end diastole $ED_1$ and becomes "0" in the end diastole $ED_1$.

The position correction section 14 applies the first weighting function $W_0(t)$ to the contour position $P_0(t)$ and the second weighting function $W_1(t)$ to the contour position $P_1(t)$. Then, the position correction section 14 obtains the contour position P(t) in each cardiac phase within one heartbeat by adding the contour position $P_0(t)$ weighted by the first weighting function $W_0(t)$ and the contour position $P_1(t)$ weighted by the second weighting function $W_1(t)$.

In other words, the position correction section 14 obtains the contour position P(t) according to the following formula:

Contour position $P(t)=P_0(t) \times W_0(t)+P_1(t) \times W_1(t)$

Here, $W_0(t)+W_1(t)=1.0$

When the contour position P(t) in each cardiac phase within one heartbeat is obtained as described above, the image processor 10 outputs the contour position P(t) in each cardiac phase to motion-information calculator 20 and the display controller 7. The above explanation describes the endocardial contour position P(t). The image processor 10 obtains the epicardial contour position using a similar method to output the epicardial contour position to the motion-information calculator 20 and the display controller 7.

In other words, the image processor 10 outputs the coordinate information of each point composing the two-dimensional contour of the endocardium in each cardiac phase and the coordinate information of each point composing the two-dimensional contour of the epicardium in each cardiac phase to the motion-information calculator 20 and the display controller 7.

(Motion-Information Calculator 20)

The motion-information calculator 20 receives the coordinate information of each point composing the two-dimensional contour of the endocardium in each cardiac phase and the coordinate information of each point composing the two-dimensional contour of the epicardium in each cardiac phase from the image processor 10 and obtains the myocardial wall-motion information.

As one example, the motion-information calculator 20 obtains the ratio of change in wall thickness (transversal strain (%)) in the direction of wall thickness in each cardiac phase based on the coordinate information of each point composing the two-dimensional contour of the endocardium and the coordinate information of each point composing the two-dimensional contour of the epicardium in each cardiac phase. The ratio of change in wall thickness is defined as the strain in the direction of thickness between the endocardium and the epicardium. The motion-information calculator 20 may obtain a strain rate (transversal strain rate (1/s)) representing the time derivative of the ratio of change in wall thickness.

For example, the motion-information calculator 20 obtains a virtual line that is perpendicular to the endocardial contour at a point on the endocardial contour. Then, the motion-information calculator 20 obtains the point at which the virtual line crosses the epicardial contour. The motion-information calculator 20 obtains the ratio of change in wall thickness between the endocardium and the epicardium in each cardiac phase based on the distance between the point on the endocardial contour and the point on the epicardial contour in each cardiac phase. Moreover, the motion-information calculator 20 obtains the ratio of change in wall thickness for each predetermined interval in the endocardial contour and the epicardial contour. In other words, the motion-information calculator 20 obtains the ratio of change in wall thickness at a plurality of locations in the endocardium and epicardium of the heart. In this way, the motion-information calculator 20 obtains the ratio of change in wall thickness at each location of the myocardium for each cardiac phase. Moreover, the motion-information calculator 20 may obtain the strain rate for each cardiac phase by obtaining the time derivative of the ratio of change in wall thickness at each location in each cardiac phase. Then, the motion-information calculator 20 outputs the wall-motion information of each location in each cardiac phase to the display controller 7. The motion-information calculator 20 is one example of a "motion-information calculator" of this invention.

(Display Controller 7)

The display controller 7 comprises a marker generator 71 and a color assignment section 72 and causes the display 81 to display ultrasonic images.

(Marker Generator 71)

The marker generator 71 generates an endocardium marker representing the shape of the endocardial contour based on the coordinate information of the two-dimensional contour of the endocardium specified by the operator. In the same way, the marker generator 71 generates an epicardium marker representing the shape of the epicardial contour based on the coordinate information of the two-dimensional contour of the epicardium specified by the operator.

The display controller 7 causes the display 81 to display a cross-sectional image based on the cross-sectional image data in which the initial contour has been specified. Furthermore, the display controller 7 identifies the display position of each marker on the cross-sectional image based on the coordinate information of each marker and superimposes the endocardium marker and the epicardium marker on the cross-sectional image and causes the display 81 to display the same.

Moreover, upon receiving the coordinate information of each point composing the two-dimensional contour of the endocardium in each cardiac phase from the image processor 10, the marker generator 71 generates an endocardium marker representing the shape of the endocardial contour in each cardiac phase. In the same way, upon receiving the coordinate information of each point composing the two-dimensional contour of the epicardium in each cardiac phase, the marker generator 71 generates an epicardium marker representing the shape of the epicardial contour in each cardiac phase.

The display controller 7 sequentially causes the display 81 to display cross-sectional images based on the cross-sectional image data acquired in each cardiac phase for each cardiac phase. Furthermore, the display controller 7 identifies the display position of the endocardium marker in the cross-sectional images based on the coordinate information of the endocardium marker in each cardiac phase, superimposes the endocardium marker in each cardiac phase over the cross-sectional image of each cardiac phase, and sequentially causes the display 81 to display the same. In the same way, the display controller 7 identifies the display position of the epicardium marker in the cross-sectional images based on the coordinate information of the epicardium marker in each cardiac phase, superimposes the epicardium marker in each cardiac phase over the cross-sectional image of each cardiac phase, and sequentially causes the display 81 to display the same. Then, the display controller 7 sequentially updates the cross-sectional image and the markers and causes the display 81 to display the same.

(Color Assignment Section 72)

The color assignment section 72 determines a color corresponding to the degree of the wall-motion information at each location obtained by the motion-information calculator 20 and assigns different colors to each location according to the degree. For example, colors to be assigned for the degree of each ratio of change in wall thickness are determined in advance. Then, a table associating degrees of the ratio of change in wall thickness with the colors is prepared in advance and stored in a storage (not shown). In this table, different colors are associated with different degrees of the ratio of change in wall thickness. The color assignment section 72 refers to this table to determine the color corresponding to the degree of the ratio of change in wall thickness of each location in each cardiac phase and assign a color to each location.

The display controller 7 assigns the colors determined by the color assignment section 72 to each location of the myocardium displayed in the cross-sectional images of each cardiac phase and causes the display 81 to display the same. For example, the display controller 7 assigns the colors determined by the color assignment section 72 to each location in the region between the endocardium marker and the epicardium marker and causes the display 81 to display the same. The display controller 7 assigns the colors determined for each location to an area within a range with a predetermined width from each location and causes the display 81 to display the same. Then, the display controller 7 sequentially in each cardiac phase updates the cross-sectional image, the endocardium marker representing the endocardial contour, the epicardium marker representing the epicardial contour, and the wall-motion information acquired in each cardiac phase and causes the display 81 to display the same. The display 7 is one example of a "display controller" of this invention.

(Third Tracking Section 13)

In step S04 described above, if corrections of the tracking results during diastole are necessary, the retracking process (ReTrack2 function) described in Japanese Patent Application 2008-114854 may be executed. This retracking process is executed by the third tracking section 13. The third tracking section 13 receives coordinate information indicating the position of a contour corrected in an arbitrary cardiac phase. Then, the third tracking section 13 performs pattern matching (ST processing) using the speckle pattern for cross-sectional images following the arbitrary cardiac phase using the corrected contour as the initial contour in order to obtain the position of the contour in each cardiac phase following the arbitrary cardiac phase.

First, using the operating section 82, the operator issues an instruction for a correction and the instruction is output to the controller 9. The controller 9 issues the correction instruction to the image processor 10. Then, using the operating section 82, the operator specifies an arbitrary cardiac phase in which to correct the endocardial contour position or the epicardial contour position. The display controller 7 causes the display 81 to display a cross-sectional image based on the cross-sectional image data acquired in the specified cardiac phase.

For example, when correcting the endocardial contour position, the operator uses the operating section 82 and refers to the endocardium represented in the cross-sectional image to specify a new two-dimensional contour of the endocardium. As an example, the operator compares the endocardial contour position represented in the cross-sectional image with the contour position obtained through the ST process performed by the first tracking section 11 to judge whether the tracking position has deviated or is aligned. The endocardial contour position obtained through the ST process performed by the first tracking section 11 is represented on the cross-sectional image by the endocardium marker. For this reason, the operator may judge whether a correction has been made by comparing the position of the endocardium marker with the position of the endocardial contour represented in the cross-sectional image. Regarding the epicardium as well, the operator judges whether a correction has been made by comparing the position of the epicardium marker with the position of the epicardial contour represented in the cross-sectional image.

Then, the operator uses the operating section 82 and refers to the endocardial contour represented in the cross-sectional image to correct the position of the endocardial contour obtained through the ST process performed by the first tracking section 11 to the expected position.

For example, the operator uses the operating section 82 to specify a new contour position of the endocardium. In this way, when the new contour position of the endocardium is specified, coordinate information indicating the new contour position it output from the user interface (UI) 8 to the image processor 10 through the controller 9. The third tracking section 13 defines the new contour of the endocardium as the initial contour to be tracked. Then, the third tracking section 13 performs ST processing for the cross-sectional images following the specified cardiac phase in order to obtain the endocardial contour position subsequent to that cardiac phase.

When correcting the epicardial contour position, the operator uses the operating section 82 to specify a new contour position of the epicardium. The third tracking section 13 defines the new contour of the epicardium as the initial contour to be tracked. Then, the third tracking section 13 obtains the epicardial contour position subsequent to a cardiac phase specified by the operator. The third tracking section 13 outputs the coordinate information of the contour in each cardiac phase following the cardiac phase specified by the operator to the position correction section 14.

On the other hand, when the operator issues an instruction for retracking, the coordinate information of the contours in each cardiac phase preceding the cardiac phase specified by the operator is output from the first tracking section 11 to the position correction section 14 and the coordinate information is retained in the position correction section 14. Specifically, the first tracking section 11 outputs coordinate information indicating the endocardial contour position and coordinate information indicating the epicardial contour position in each cardiac phase preceding the cardiac phase specified by the operator to the position correction section 14. The position correction section 14 retains the endocardial contour position in each cardiac phase and the epicardial contour position in each cardiac phase.

The position correction section 14 retains the coordinate information of the contours in each cardiac phase preceding the cardiac phase specified by the operator. Furthermore, the position correction section 14 receives the coordinate information of the contours that have been retracked by the third tracking section 13 from the third tracking section 13. Then, the position correction section 14 obtains the position of the contours in all time phases based on the coordinate information of the contours before the cardiac phase for which the operator has specified a correction and the coordinate information of the retracked contours. It is preferable that the position correction section 14 smoothens the contour position in the temporal direction in the cardiac phase for which a correction has been specified in order to smoothly connect the contours near the specified cardiac phase.

Then, the display controller 7 superimposes the endocardium marker and the epicardium marker over the cross-sectional image in each cardiac phase and causes the display 81 to display the same in the order of cardiac phases.

For example, in the cardiac phase E' during diastole, when the endocardial contour position determined through ST processing deviates from the tracking, the endocardial contour position determined through ST processing during diastole is corrected. When the operator uses the operating section 82 to specify the cardiac phase E', the display controller 7 causes the display 81 to display the cross-sectional image from the cardiac phase E'. The operator compares the endocardium represented in the cross-sectional image in the cardiac phase E' with the endocardial contour (endocardium marker) determined through ST processing to correct the endocardial contour position determined through ST processing. In other words, the operator uses the operating section 82 to specify the new contour position of the endocardium. When a new contour position of the endocardium is thus specified by the operator, coordinate information indicating the new contour position is output from the user interface (UI) 8 to the third tracking section 13 through the controller 9. Then, the new contour position is set as the initial endocardial contour in the third tracking section 13.

By defining the newly specified endocardial contour as the initial contour, the third tracking section 13 performs an ST process for each item of cross-sectional image data acquired subsequent to the cardiac phase E' to obtain the endocardial contour position in each cardiac phase following the cardiac phase E'. In this way, the endocardial contour position is updated. Then, the third tracking section 13 outputs the coordinate information of the endocardial contour position in each cardiac phase following the cardiac phase E' to the position correction section 14.

On the other hand, when the operator issues an instruction for retracking, coordinate information of the contour in each cardiac phase preceding the cardiac phase specified by the operator is output from the first tracking section 11 to the position correction section 14 and the coordinate information is retained in the position correction section 14. As an example, coordinate information indicating the endocardial contour position in each cardiac phase preceding the cardiac phase E' is retained in the position correction section 14.

Then, the position correction section 14 obtains the endocardial contour position over one heartbeat by connecting in cardiac phase E' the endocardial contour position in each cardiac phase preceding the cardiac phase E' with the endocardial contour position in each cardiac phase following cardiac phase E'. Furthermore, the position correction section 14 smoothens the contour position in the temporal direction in the cardiac phase E' in order to smoothly connect the contour positions.

Then, the image processor 10 outputs the coordinate information of the contour to the display controller 7 and the motion-information calculator 20. As described above, the marker generator 71 generates a contour marker in each cardiac phase based on the coordinate information of the contour in each cardiac phase. Moreover, the motion-information calculator 20 obtains the wall-motion information in each cardiac phase based on the coordinate information of the contour in each cardiac phase. Then, the display controller 7 sequentially updates the cross-sectional image, the marker, and the wall-motion information and causes the display 81 to display the same.

Through the above processes, the operator is able to automatically and easily acquire a more accurate tracking position during systole in a subject heartbeat period through a tracking process simply by specifying the first initial contour position IC1 and the second initial contour position IC2. In this way, it becomes possible to acquire more accurate wall-motion information through simply operations.

In the example described above, the operational procedures performed by the operator may be reduced to the full extent possible by automatically displaying an ultrasonic image from the end diastole $ED_0$ in step S02 and automatically displaying an ultrasonic image from the end systole ES in step S03. In other words, because it is not necessary to make manual selections of the cardiac phase, it is possible to reduce the number of operational procedures performed by the operator.

In this illustrative embodiment, the process of step S04 described above has a characteristic. Specifically, the controlling of the tracking results to pass through the positions of a plurality of initial contours set by the operator to the extent possible is a characteristic of the ultrasonic imaging apparatus 1 related to this illustrative embodiment. By setting the position of the initial contour in the two time phases of the end diastole and the end systole in step S02 and step S03, tracking errors during systole are reduced and it becomes possible to provide tracking results that are more accurate than those obtained through ST processes related to existing technology in which the initial contour is set in only one time phase.

Furthermore, when tracking errors are discovered in the diastolic tracking results, by executing a retracking process (ReTrack2 function) using the third tracking section 13, it becomes possible to acquire more accurate tracking results even in cardiac phases following diastole.

Modified Example 1

In the first illustrative embodiment described above, the operator specifies the initial contour twice. Consequently, compared to existing technology, the operational procedure increases by one step and the operations may become troublesome. Therefore, the operational procedure performed by the operator may be reduced by automatically detecting and setting the position of the initial contour.

(Step S10)

First, the operator uses the operating section 82 to specify one heartbeat (cardiac phase t=end diastole $ED_0$ to the following end diastole $ED_1$). When the one heartbeat is specified, information indicating the specified cardiac phase (end diastole $ED_0$ to the following end diastole $ED_1$) is output from the user interface (UI) 8 to the image processor 10 and the display controller 7.

(Step S11)

The image processor 10 acquires cross-sectional image data of the first initial time phase $T_1$ (end diastole $ED_0$) from the storage 6 and detects the first initial contour IC1 of the endocardium.

(Step S12)

Moreover, the image processor 10 acquires cross-sectional image data of the second initial time phase $T_2$ (end systole ES) from the storage 6 and detects the second initial contour IC2 of the endocardium.

Preferred methods of automatically detecting the first initial contour position IC1 and the second initial contour position IC2 include the publicly known AQ (Acoustic Quantification) and ASM (Active Shape Model) methods. The AQ method may be, for example, the method described in "Ultrasonic Imaging 5, 300-307 (1983)".

Moreover, methods for contour detection using the ASM method are described by, for example. Cooles, et al. in "Active shape models: Their training and application" (Comput. Vis. Image Undestand., vol. 61, no. 1, pp. 38-59, January 1995). In the ASM method, a generic shape of the desired tissue is registered in advance in a shape dictionary. The image processor 10 detects the contour of the desired tissue based on the brightness information of the cross-sectional image data and the shape registered in the shape dictionary. For example, generic shapes of the endocardium and the epicardium of the heart are registered in advance in the shape dictionary. The image processor 10 detects the endocardial or epicardial contour based on the brightness information of the cross-sectional image data and the generic shape of the endocardium or the epicardium.

(Step S13)

The image processor 10 outputs coordinate information of the first initial contour position IC1 and coordinate information of the second initial contour position IC2 to the display controller 7. The display controller 7 causes the display 81 to display a cross-sectional image in the first initial time phase $T_1$, superimposes a marker representing the first initial contour position IC1 on the cross-sectional image, and causes the display 81 to display the same.

Moreover, the display controller 7 causes the display 81 to display a cross-sectional image in the second initial time phase $T_2$, superimposes a marker representing the second initial contour position IC2 on the cross-sectional image, and causes the display 81 to display the same. The operator may correct the first initial contour position IC1 and the second initial contour position IC2 by referring to the first initial contour position IC1 and the second initial contour position IC2 displayed on the display 81.

(Step S14)

The first tracking section 11 obtains the endocardial contour position $P_0(t)$ in each cardiac phase by performing ST processing with the automatically detected first initial contour position IC1 as the tracking subject. Moreover, the first tracking section 11 obtains the endocardial contour position $P_1(t)$ in each cardiac phase by performing ST processing with the automatically detected second initial contour position IC2 as the tracking subject.

Based on the endocardial contour position $P_0(t)$ in each cardiac phase and the endocardial contour position $P_1(t)$ in each cardiac phase, the position correction section 14 corrects the contour position so that it passes through the first initial contour position IC1 in the end diastole $ED_0$ and through the second initial contour position IC2 in the end systole ES, thereby obtaining the endocardial contour position $P(t)$ in each cardiac phase.

(Step S15)

Moreover, when it is necessary to correct the tracking results during diastole, a retracking process (ReTrack2 function) performed by the third tracking section 13 may be executed. In this case, the operator uses the operating section 82 to issue an instruction for the retracking process and the third tracking section 13 executes the retracking process.

Through the above process, simply by specifying the subject heartbeat period, the operator is basically able to automatically and easily acquire a more accurate tracking position during systole in a subject heartbeat period through a tracking process.

The degree of accuracy of the tracking results largely depends on the accuracy of the automatic detection of the first initial contour position IC1 and the second initial contour position IC2. Therefore, in Modified Example 1, it is desirable as described in step S13 to execute ST processing after contour positions are acquired that are confirmed by the operator and that are believed to be correct by using a correction function if necessary. In this way, the characteristics related to the first illustrative embodiment described above are maintained.

Furthermore, if a tracking error is discovered in the tracking results during diastole as described in step S15, the retracking process (ReTrack2 function) is executed, thereby acquiring more accurate tracking results even during the diastolic cardiac phase.

Modified Example 2

In the first illustrative embodiment and Modified Example 1 described above, cases in which initial contours are set in the two time phases of the end diastole ED and the end systole ES have been described. In Modified Example 2, as in existing technology, considering the fact that tracking errors tend to occur during diastole (especially after cardiac phase E'). ST processing is executed after preliminarily setting an initial contour in a third cardiac phase after cardiac phase E'. This preliminarily restrains the tracking results not only during systole but also during diastole, allowing for further improvements in the tracking accuracy of the first ST process.

Furthermore, in Modified Example 2, due to the need to set 3 initial contours, the number of steps for setting the initial contours increases by 1 step. However, due to the decrease in cases requiring a correction step during diastole using the retracking process (ReTrack2 function), the overall operational procedure does not increase greatly.

Moreover, Modified Example 2 may be applied to the first illustrative embodiment described above and may also be applied to Modified Example 1.

Second Illustrative Embodiment

Next, an ultrasonic imaging apparatus related to a second illustrative embodiment of this invention will be described. In the second illustrative embodiment, contour tracking errors during systole are corrected through retracking by sandwiching between two cardiac phases included in the systole. As an example, a case in which an initial endocardial contour and an initial epicardial contour are set during the end diastole ED in the second illustrative embodiment will be described.

In the second illustrative embodiment, the initial endocardial contour and the initial epicardial contour are set during the end diastole ED and ST processing is implemented once during the period being tracked. In cases in which a tracking error has occurred in a forward direction at some point during systole, the cardiac phase that accumulates the most tracking errors during systole and has become large is the cardiac phase of the end systole ES. Therefore, the operator corrects locations where the tracking has deviated during the end systole ES to an appropriate position.

In order to judge whether the tracking position of the endocardium has deviated or is aligned, the operator compares the endocardial contour position represented in the cross-sectional image with the endocardium marker representing the shape of the contour acquired through ST processing.

Moreover, in order to judge whether the tracking position of the epicardium has deviated or is aligned, the operator compares the epicardial contour position represented in the cross-sectional image with the epicardium marker representing the shape of the contour acquired through ST processing.

Then, with the contour position corrected by the operator as the starting point, the contour during systole is tracked in the reverse direction. Specifically, by correcting the contour position so that it passes through the position of the initial contour in the end diastole ED and the corrected contour position in the end systole ES, the contour position in each cardiac phase is obtained. Therefore, it may be expected that more accurate tracking results may be obtained during systole.

On the other hand, during diastole, when there are locations at which the tracking has deviated in the end systole ES due to the first tracking process, the tracking of the contour at those locations during diastole are all deviated. Consequently, using the corrected contour position as the starting point, by retracking the contour in the forward direction during diastole, the tracking accuracy of the contour during diastole increases compared to the first tracking results. The retracking process related to this second illustrative embodiment may also be referred to as the "ReTrack1 function".

Furthermore, when a tracking error is discovered in the tracking results during diastole, by executing the retracking process performed by the ReTrack2 function, more accurate tracking results may be easily acquired even in the diastolic cardiac phase.

A series of processes related to this second illustrative embodiment will now be described.

(Step S20)

First, using the operating section 82, the operator specifies one heartbeat (cardiac phase t=end diastole $ED_0$ to the following end diastole $ED_1$). When the one heartbeat is specified, information indicating the specified cardiac phase (end diastole $ED_0$ to the following end diastole $ED_1$) is output from the user interface (UI) 8 to the image processor 10 and the display controller 7.

(Step S21)

Next, using the operating section 82, the operator specifies the position of a first initial contour (corresponding to the first region of interest) in an initial time phase (corresponding to the first time phase).

For example, when the operator specifies the end diastole $ED_0$ as the initial time phase by using the operating section 82, the display controller 7 causes the display 81 to display a cross-sectional image of the end diastole $ED_0$. Then, using the operating section 82, the operator specifies the first initial contour position IC1 for the endocardium and the first initial contour position IC1 for the epicardium on the cross-sectional image of the end diastole $ED_0$.

(Step S22)

The first tracking section 11 defines the first initial contour position IC1 specified by the operator as the tracking subject. Then, the first tracking section 11 performs ST processing for cross-sectional image data from each cardiac phase acquired within one heartbeat (end diastole $ED_0$ to the following end diastole $ED_1$). In this way, the first tracking section 11 obtains the endocardial contour position $P_0(t)$ and the epicardial contour position $P_0(t)$ in each time phase within the one heartbeat, which includes the remaining cardiac phases. Then, the first tracking section 11 outputs the endocardial contour position $P_0(t)$ and the epicardial contour position $P_0(t)$ to the position correction section 14. Moreover, the image processor 10 outputs the endocardial contour position $P_0(t)$ and the epicardial contour position $P_0(t)$ to the motion-information calculator 20 and the display controller 7.

(Step S23)

Based on the endocardial contour position $P_0(t)$ and the epicardial contour position $P_0(t)$ obtained by the first tracking section 11, the motion-information calculator 20 calculates the wall-motion information in each cardiac phase and outputs the information to the display controller 7. The display controller 7 generates an endocardium marker in each cardiac phase based on the endocardial contour position $P_0(t)$. Moreover, the display controller 7 generates an epicardium marker in each cardiac phase based on the epicardial contour position $P_0(t)$. Then, the display controller 7 sequentially updates the cross-sectional image, endocardium marker, epicardium marker, and wall-motion information in each cardiac phase for each cardiac phase and causes the display 81 to display the same.

(Step S24)

The operator corrects the contour position determined through ST processing in regions deviated from the tracking process by referring to the cross-sectional image, motion information, and markers displayed on the display 81 and using the operating section 82. As an example, the operator compares the endocardial contour position and the epicardial contour position represented in the cross-sectional image with the endocardial contour position and the epicardial contour position obtained through ST processing by the first tracking section 11 to judge whether the tracking position has deviated or is aligned.

Then, using the operating section 82, the operator corrects the endocardial contour position or the epicardial contour position to specify a new contour position. When a new contour position for the endocardium or a new contour position for the epicardium is thus specified, coordinate information indicating the new contour information is output from the user interface (UI) 8 to the image processor 10 through the controller 9 and set in the second tracking section 12.

In the second illustrative embodiment, the operator judges that tracking of the contour position has deviated in the cardiac phase $T_1$ (end systole ES) (corresponding to the second time phase) and corrects the contour position in the cardiac phase $T_1$ (end systole ES). In this way, a new contour position that has been corrected in the cardiac phase $T_1$ (end systole ES) is set in the second tracking section 12. The second tracking section 12 sets the new contour position corrected in the cardiac phase $T_1$ (end systole ES) as the second initial contour position IC2 (corresponding to the second region of interest).

(Step S25)

The second tracking section 12 defines the second initial contour position IC2 set in the cardiac phase $T_1$ (end systole ES) as the tracking subject. Then, the second tracking section 12 performs ST processing for cross-sectional image data of each cardiac phase acquired from the cardiac phase $T_1$ (end systole ES) to the end diastole $ED_0$. In this way, the second tracking section 12 obtains the endocardial contour position $P_1(t)$ and the epicardial contour position $P_1(t)$ in each cardiac phase in the period from the cardiac phase $T_1$ (end systole ES) to the end diastole $ED_0$. In other words, the second tracking section 12 obtains the contour position $P_1(t)$ by performing the tracking process in the reverse direction from the cardiac phase $T_1$ (end systole ES) to the end diastole $ED_0$ of the initial time phase.

Moreover, the second tracking section 12 defines the second initial contour position IC2 set in the cardiac phase $T_1$ (end systole ES) as the tracking subject. Then, the second tracking section 12 performs ST processing for cross-sectional image data of each cardiac phase acquired from the cardiac phase $T_1$ (end systole ES) to the following end diastole $ED_1$. In this way, the second tracking section 12 obtains the endocardial contour position $P_2(t)$ and the epicardial contour position $P_2(t)$ of each cardiac phase from the cardiac phase $T_1$ (end systole ES) to the end diastole $ED_1$. In other words, the second tracking section 12 performs the tracking process in the forward direction from the cardiac phase $T_1$ (end systole ES) to the following end diastole $ED_1$. In this way, the second tracking section 12 obtains the endocardial and epicardial contour positions (contour position $P_1(t)$ and contour position $P_2(t)$) in each cardiac phase within one heartbeat. Then, the second tracking section 12 outputs the contour position $P_1(t)$ and the contour position $P_2(t)$ to the position correction section 14. The second tracking section 12 corresponds to a "second tracking part" of this invention.

(Step S26)

Based on the contour position $P_0(t)$ and the contour position $P_1(t)$, the position correction section 14 obtains the endocardial contour position P(t) and the epicardial contour position P(t) in each cardiac phase included in the period (systole) from the initial time phase (end diastole $ED_0$) to the cardiac phase $T_1$ (end systole ES) so that they pass through the first initial contour position IC1 in the end diastole $ED_0$ and through the second initial contour position IC2 in the cardiac phase $T_1$ (end systole ES).

The contour position $P_0(t)$ is the contour position acquired by the first tracking section 11 using the first initial contour position IC1 as the tracking subject. The contour position $P_0(t)$ represents the contour position in the period from the initial time phase (end diastole $ED_0$) to the cardiac phase $T_1$ (end systole ES).

The contour position $P_1(t)$ is the contour position acquired by the second tracking section 12 using the second initial contour position IC2 as the tracking subject. The contour position $P_1(t)$ represents the contour position in the period from the cardiac phase $T_1$ (end systole ES) to the initial time phase (end diastole $ED_0$).

(Step S27)

Furthermore, the position correction section 14 updates the contour position from the cardiac phase $T_1$ (end systole ES) to the end diastole $ED_1$ by using the contour position $P_2(t)$ obtained by the second tracking section 12.

(Step S28)

Moreover, when a correction is required for the contour position $P_2(t)$, which is a result of tracking during diastole, a retracking process (ReTrack2 function) performed by the third tracking section 13 may be executed.

In the above step S26, the position correction section 14 obtains the contour position P(t) in each cardiac phase included in the period (systole) from the end diastole $ED_0$ to the end systole ES according to the first method or the second method described above.

In other words, when the first method is followed, the position correction section 14 connects the contour position $P_0(t)$ and the contour position $P_1(t)$ in the cardiac phase tm between the end diastole $ED_0$ and the end systole ES. In this way, the position correction section 14 obtains the contour position P(t) in each cardiac phase included in the period from the end diastole $ED_0$ to the end systole ES. It is preferable that the position correction section 14 implements a smoothing process of the contour position or a fitting process of the contour position in the temporal direction near the cardiac phase tm as described above.

When the second method is followed, the position correction section 14 performs weighting according to time for the contour position $P_0(t)$ and the contour position $P_1(t)$ and adds the two positions. In this way, the position correction section 14 obtains the contour position P(t) in each cardiac phase included in the period from the end diastole $ED_0$ to the end systole ES.

Figure 2:
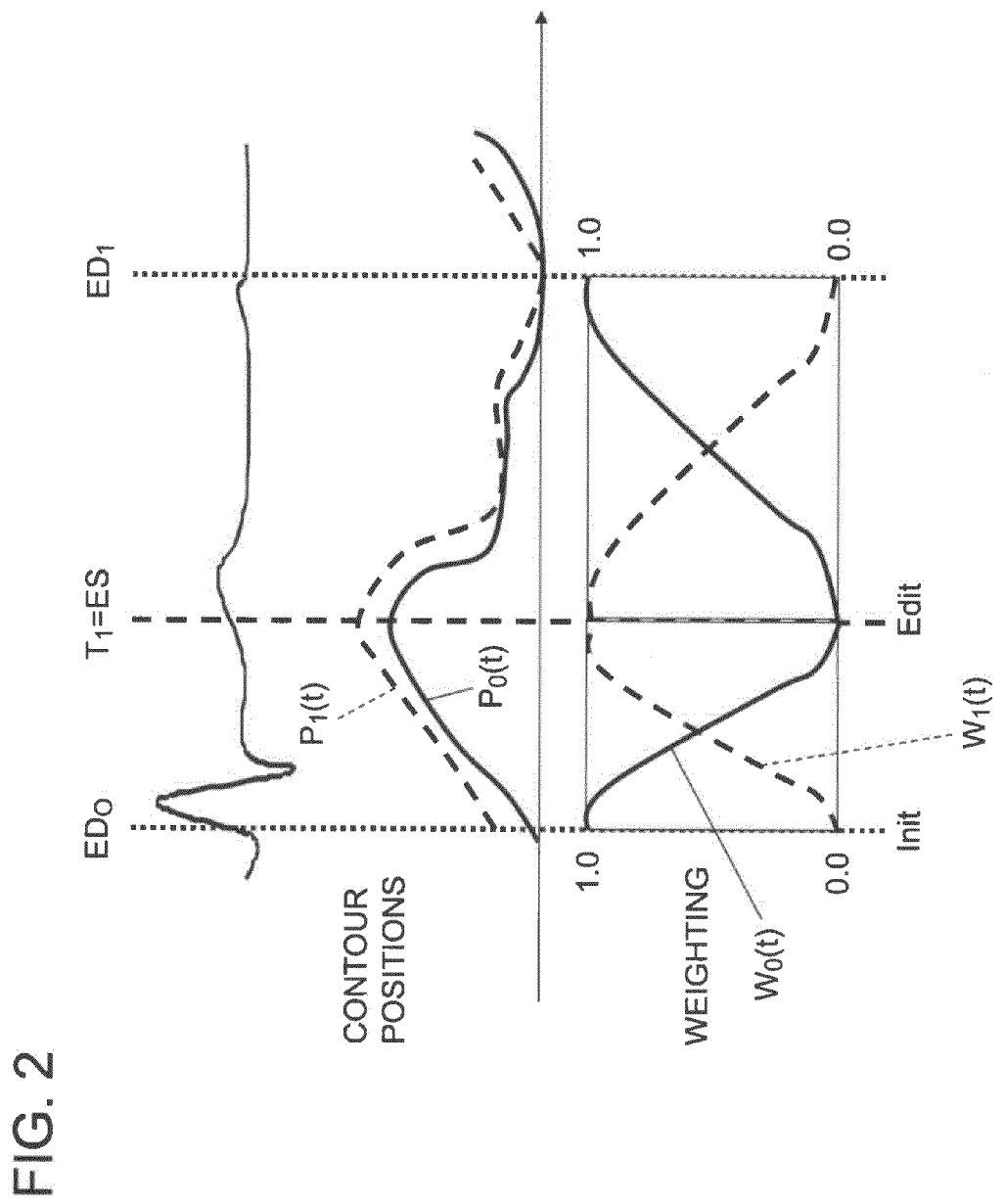
FIG. 2 is an explanatory diagram of a weighting process related to an illustrative embodiment of this invention.

A specific example of the second method will now be described with reference to FIG. 2.

For example, for the contour position $P_0(t)$, the first weighting function $W_0(t)$ is applied. The first weighting function $W_0(t)$ is a weighting function in which the weighting becomes "1" in the end diastole $ED_0$ and gradually decreases as time progresses from the end diastole $ED_0$ to the end systole ES to become "0" in the end systole ES.

For the contour position $P_1(t)$, the second weighting function $W_1(t)$ is applied. The second weighting function $W_1(t)$ is a weighting function in which the weighting becomes "0" in the end diastole $ED_0$ and gradually increases as time progresses from the end diastole $ED_0$ to the end systole ES to become "1" in the end systole ES.

The position correction section 14 applies the first weighting function $W_0(t)$ to the contour position $P_0(t)$ and applies the second weighting function $W_1(t)$ to the contour position $P_1(t)$. Then, the position correction section 14 obtains the contour position P(t) in each cardiac phase in one heartbeat by adding the contour position $P_0(t)$ weighted by the first weighting function $W_0(t)$ and the contour position $P_1(t)$ weighted by the second weighting function $W_1(t)$.

In other words, the position correction section 14 obtains the contour position P(t) according to the following formula.

Contour position $P(t) = P_0(t) \times W_0(t) + P_1(t) \times W_1(t)$

Here, $W_0(t) + W_1(t) = 1.0$

Figure 3:
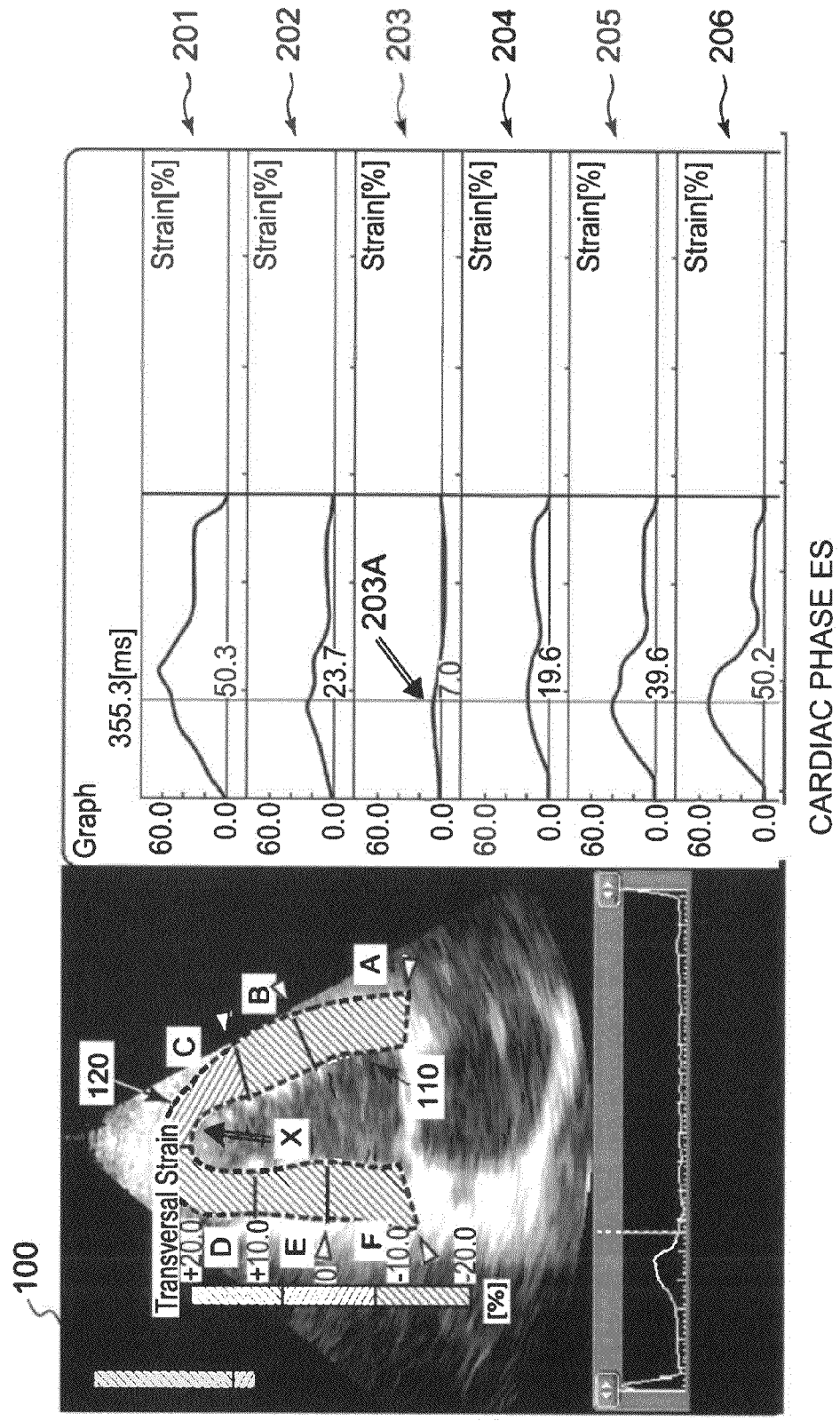
FIG. 3 is a diagram showing an image acquired by an ultrasonic imaging apparatus related to a second illustrative embodiment of this invention as well as wall-motion information.

A specific example of the second illustrative embodiment will be described with reference to FIGS. 3-6. A case in which a longitudinal image is acquired and displayed using the second illustrative embodiment will be described. First, the processes from step S20 to step S22 described above are implemented. FIG. 3 shows the processing results up to step S22.

As an example, the display controller 7 causes the display 81 to display a longitudinal image 100. Furthermore, the display controller 7 superimposes an endocardium marker 110 and an epicardium marker 120 on the longitudinal image 100 and causes the display 81 to display the same.

The longitudinal image 100 shown in FIG. 3 is a cross-sectional image acquired in the cardiac phase ES (end systole). Moreover, the display controller 7 causes the display 81 to display wall-motion information obtained by the motion-information calculator 20.

As an example, the display controller 7 causes the display 81 to display graphs 201-206.

Graph 201 is a graph showing changes over time in the ratio of change in wall thickness (transversal strain (%)) in region A of the myocardium.

Graph 202 is a graph showing the ratio of change in wall thickness in region B.

Graph 203 is a graph showing the ratio of change in wall thickness in region C.

Graph 204 is a graph showing the ratio of change in wall thickness in region D.

Graph 205 is a graph showing the ratio of change in wall thickness in region E.

Graph 206 is a graph showing the ratio of change in wall thickness in region F.

In graphs 201-206, the horizontal axis indicates the cardiac phase while the vertical axis indicates the ratio of change in wall thickness (%) in the longitudinal axis.

In the example shown in FIG. 3, the tracking position of the endocardium in the apical region of the anterior wall (location indicated by arrow X and arrow 203A) in the cardiac phase ES (end systole) has deviated and the strain value in this region is underestimated. Moreover, the display controller 7 assigns colors corresponding to the wall-motion information to each location in the range between the endocardium and the epicardium represented in the longitudinal image 100 and causes the display 81 to display the same.

For example, the display controller 7 assigns colors corresponding to the degree of the ratio of change in wall thickness to each location between the endocardium marker 110 and the epicardium marker 120, superimposes the colors on the longitudinal image 100, and causes the display 81 to display the same.

Figure 4:
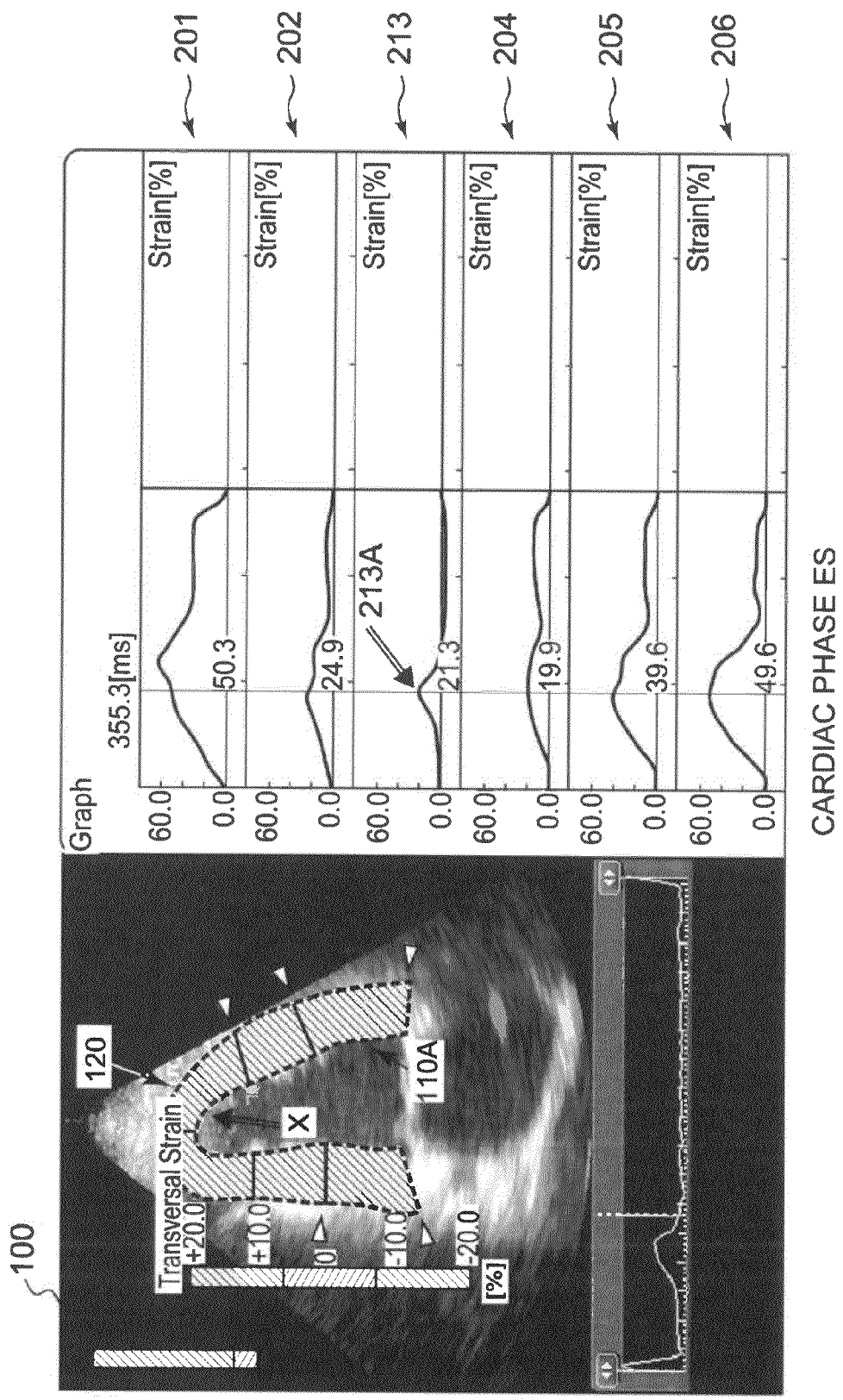
FIG. 4 is a diagram showing an image acquired by an ultrasonic imaging apparatus related to a second illustrative embodiment of this invention as well as wall-motion information.

FIG. 4 shows a state in which the contour position of the apical region of the anterior wall has been corrected in step S24. FIG. 4 shows the corrected endocardium marker 110A. Moreover, the values of graph 203 (location indicated by arrow 213A) are also corrected according to this correction operation and displayed as graph 213.

Figure 5:
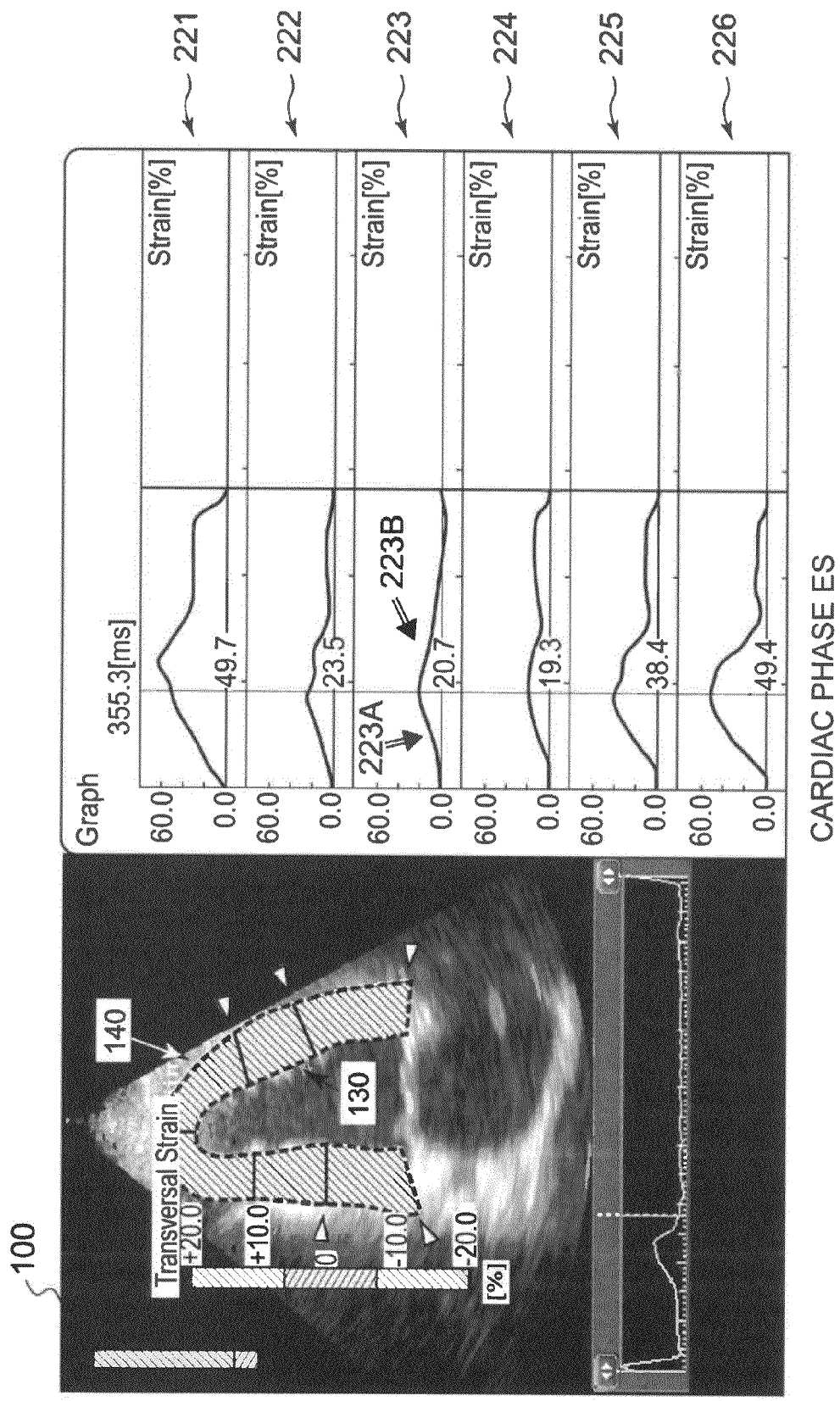
FIG. 5 is a diagram showing an image acquired by an ultrasonic imaging apparatus related to a second illustrative embodiment of this invention as well as wall-motion information.

Next, FIG. 5 shows a state in which the processes from step S25 to step S27 have been implemented. The contour position of the apical region of the anterior wall during systole and the contour position of the apical region of the anterior wall during diastole are updated and a new endocardium marker 130 and epicardium marker 140 are displayed.

Furthermore, graphs of the ratios of change in wall thickness are updated to graphs 221-226 and displayed. In the period including the cardiac phase ES (end systole), the ratios of change in wall thickness is represented more accurately (locations indicated by arrow 223A and arrow 223B).

Figure 6:
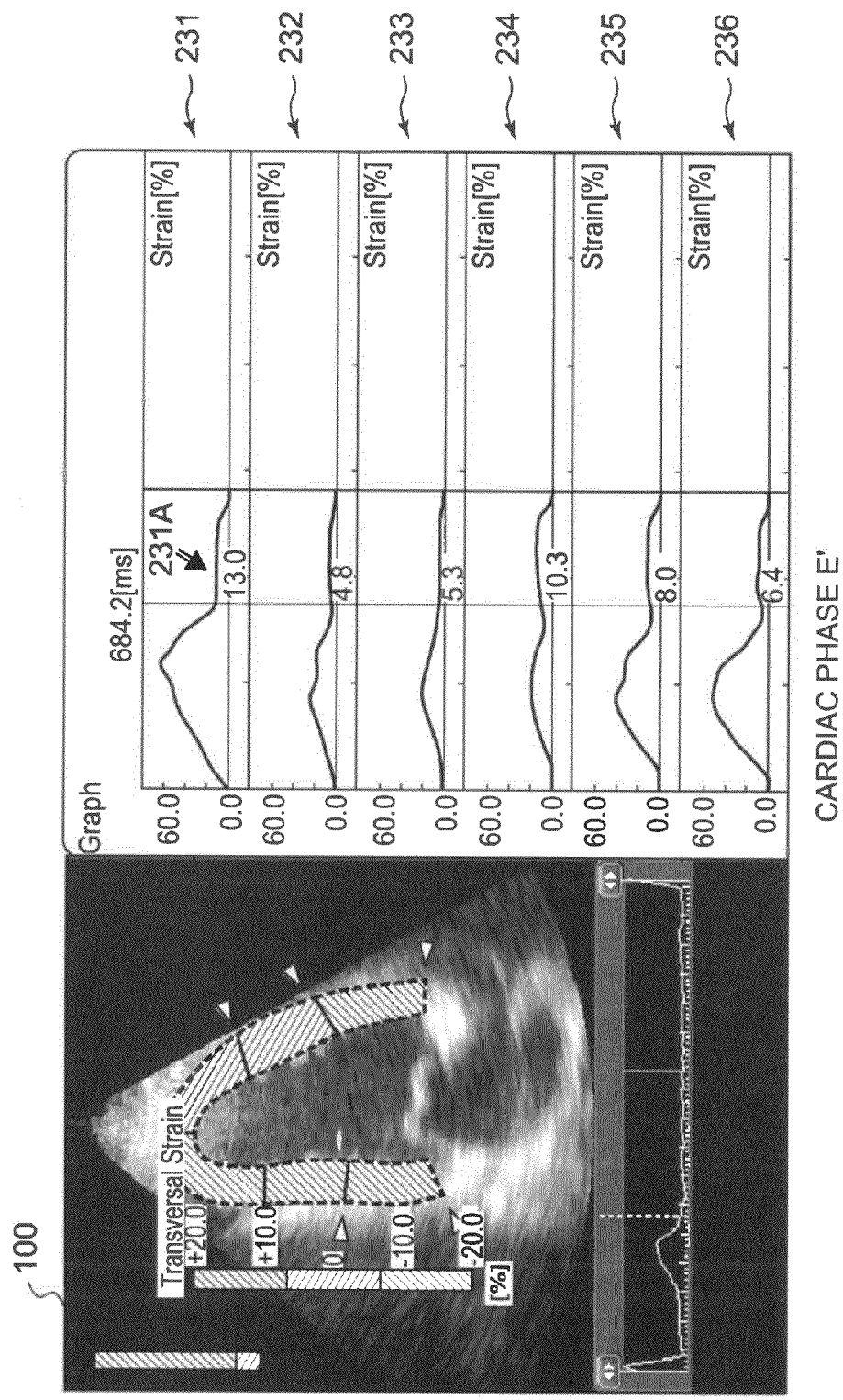
FIG. 6 is a diagram showing an image acquired by an ultrasonic imaging apparatus related to a second illustrative embodiment of this invention as well as wall-motion information.

Furthermore, in the example shown in FIG. 5, a tracking deviation has occurred after the cardiac phase E' during tracking in the anterior wall ring region during diastole. For this reason, the retracking process (ReTrack2 function) performed by the third tracking section 13 has been executed. FIG. 6 shows the state after the ReTrack2 function has been executed. FIG. 6 shows graphs 231-236 of the state after the retracking process performed by the third tracking section 13.

As a result of this retracking process, tracking deviations are resolved and the ratios of change in wall thickness are evaluated more accurately.

For example, as with the location indicated by arrow 231A in graph 231, the ratio of change in wall thickness is evaluated accurately.

Third Illustrative Embodiment

Next, an ultrasonic imaging apparatus of a third illustrative embodiment of this invention will be described. The third illustrative embodiment describes, as the second illustrative embodiment, correction of contour tracking errors during systole through retracking by sandwiching between two cardiac phases included in the systole. As an example, a case will be described in which an initial endocardial contour and an initial epicardial contour are set during the end systole ES in the third illustrative embodiment.

In the third illustrative embodiment, the initial endocardial contour and the initial epicardial contour are set during the end systole ES and ST processing is implemented once in the period of tracking. If a tracking error occurs in the reverse direction at a point during systole, the systolic cardiac phase in which the most tracking errors are accumulated to become large is the time phase of the end diastole ED.

Therefore, the operator corrects to an appropriate position the locations deviating from tracking during the end diastole ED.

Here, in order to judge whether the tracking position of the endocardium has deviated or is aligned, the operator compares the endocardial contour position represented in the cross-sectional image with the endocardium marker representing the shape of the contour acquired through ST processing.

Moreover, in order to judge whether the tracking position of the epicardium has deviated or is aligned, the operator compares the epicardial contour position represented in the cross-sectional image with the epicardium marker representing the shape of the contour acquired through ST processing.

Then, the contour during systole is tracked in the forward direction using the operator-corrected contour position as the starting point. Specifically, the contour position in each cardiac phase is obtained by correcting the contour position so that it passes through the initial contour position in the end systole ES and through the corrected contour position in the end diastole ED. In this way, more accurate tracking results may be acquired during systole. On the other hand, during diastole, unlike the second illustrative embodiment, because tracking is performed using the initial contour set in the end systole ES as the starting point, there is no need to update the tracking results and the first tracking results are maintained. The retracking process related to this third illustrative embodiment, like the retracking process related to the second illustrative embodiment, may also be referred to as the "ReTrack1 function".

Furthermore, when a tracking error is discovered in the first tracking results during diastole, by executing the retracking process using the ReTrack2 function, more accurate tracking results may be easily acquired even during the diastolic cardiac phase.

A series of processes related to this third illustrative embodiment will now be described.
(Step S30)

First, using the operating section 82, the operator specifies one heartbeat (cardiac phase t=end diastole $ED_0$ to the following end diastole $ED_1$). When the one heartbeat is specified, information indicating the specified cardiac phase (end diastole $ED_0$ to the following end diastole $ED_1$) is output from the user interface (UI) 8 to the image processor 10 and the display controller 7.
(Step S31)

Next, using the operating section 82, the operator specifies the position of a first initial contour (corresponding to the first region of interest) in an initial time phase (corresponding to the first time phase).

For example, when the operator specifies the end systole ES as the initial time phase by using the operating section 82, the display controller 7 causes the display 81 to display a cross-sectional image in the end systole ES. Then, using the operating section 82, the operator specifies the first initial contour position IC1 of the endocardium and the first initial contour position IC1 of the epicardium on the cross-sectional image in the end systole ES.
(Step S32)

The first tracking section 11 defines the first initial contour position IC1 specified by the operator as the tracking subject. Then, the first tracking section 11 performs ST processing for cross-sectional image data in each cardiac phase acquired within one heartbeat (end diastole $ED_0$ to the following end diastole $ED_1$). In this way, the first tracking section 11 obtains the endocardial contour position $P_0(t)$ and the epicardial contour position $P_0(t)$ in each cardiac phase within the one heartbeat, which includes the remaining cardiac phases. Then, the first tracking section 11 outputs the endocardial contour position $P_0(t)$ and the epicardial contour position $P_0(t)$ to the position correction section 14. Moreover, the image processor 10 outputs the endocardial contour position $P_0(t)$ and the epicardial contour position $P_0(t)$ to the motion-information calculator 20 and the display controller 7.
(Step S33)

Based on the endocardial contour position $P_0(t)$ and the epicardial contour position $P_0(t)$ obtained by the first tracking section 11, the motion-information calculator 20 calculates wall-motion information of each cardiac phase and outputs the same to the display controller 7. The display controller 7 generates an endocardium marker and an epicardium marker in each cardiac phase based on the endocardial contour position $P_0(t)$ and the epicardial contour position $P_0(t)$. Then, the display controller 7 sequentially updates the cross-sectional image, the endocardium marker, the epicardium marker, and the wall-motion information of each cardiac phase for each cardiac phase and causes the display 81 to display the same.
(Step S34)

The operator refers to the cross-sectional image, motion information, and markers displayed on the display 81, in order to correct the contour position in regions deviating from the tracking process, through ST processing with the operating section 82. As one example, the operator compares the endocardial contour position and the epicardial contour position represented in the cross-sectional image with the endocardial contour position and the epicardial contour position obtained through ST processing performed by the first tracking section 11 to judge whether the tracking position has deviated or is aligned. Then, using the operating section 82, the operator corrects the endocardial contour position or the epicardial contour position to specify a new contour position. When a new contour position of the endocardium or the epicardium is thus specified, coordinate information indicating the new contour position is output from the user interface (UI) 8 to the image processor 10 through the controller 9 and is set in the second tracking section 12.

In the third illustrative embodiment, the operator judges that the tracking of the contour position has deviated in the cardiac phase $T_1$ (end diastole $ED_0$) (corresponding to the second time phase) and corrects the contour position in the cardiac phase $T_1$ (end diastole $ED_0$).

In this way, the new contour position corrected in the cardiac phase $T_1$ (end diastole $ED_0$) is set in the second tracking section 12.

The second tracking section 12 sets the new contour position corrected in the cardiac phase $T_1$ (end diastole $ED_0$) as the second initial contour position IC2 (corresponding to the second region of interest).

(Step S35)

The second tracking section 12 defines the second initial contour position IC2 set in the cardiac phase $T_1$ (end diastole $ED_0$) as the tracking subject. Then, the second tracking section 12 performs ST processing for cross-sectional image data of each cardiac phase acquired from the cardiac phase $T_1$ (end diastole $ED_0$) to the end systole ES in order to obtain the endocardial contour position $P_1(t)$ and the epicardial contour position $P_1(t)$ in each cardiac phase in the period from the cardiac phase $T_1$ (end diastole $ED_0$) to the end systole ES. In other words, the second tracking section 12 obtains the contour position $P_1(t)$ by performing the tracking process in the forward direction from the cardiac phase $T_1$ (end diastole $ED_0$) to the end systole ES, which is the initial time phase. Then, the second tracking section 12 outputs the contour position $P_1(t)$ to the position correction section 14.

(Step S36)

Based on the contour position $P_0(t)$ and the contour position $P_1(t)$, the position correction section 14 obtains the endocardial contour position P(t) and the epicardial contour position P(t) in each cardiac phase included in the period (systole) from the cardiac phase $T_1$ (end diastole $ED_0$) to the initial time phase (end systole ES) so that the positions pass the second initial contour position IC2 in the cardiac phase $T_1$ (end diastole $ED_0$) and the first initial contour position IC1 in the end systole ES.

The contour position $P_0(t)$ is a contour position acquired by the first tracking section 11 by setting the first initial contour position IC1 as the tracking subject. Moreover, the contour position $P_0(t)$ represents the contour position in the period from the initial time phase (end systole ES) to the cardiac phase $T_1$ (end diastole $ED_0$).

The contour position $P_1(t)$ is a contour position acquired by the second tracking section 12 by setting the second initial contour position IC2 as the tracking subject. Moreover, the contour position $P_1(t)$ represents the contour position in the period from the cardiac phase $T_1$ (end diastole $ED_0$) to the initial time phase (end systole ES).

(Step S37)

Furthermore, for the diastole from the initial time phase (end systole ES) to the end diastole $ED_1$, the image processor 10 maintains the contour position $P_0(t)$ obtained by the first tracking section 11 in step S32.

(Step S38)

Moreover, when it is necessary to correct the contour position $P_0(t)$, which is a tracking result during diastole, the retracking process (ReTrack2 function) performed by the third tracking section 13 may be executed.

In the above step S36, according to the first method or the second method as in the second illustrative embodiment, the position correction section 14 obtains the contour position P(t) in each cardiac phase included in the period (systole) from the end diastole $ED_0$ to the end systole ES.

Figure 7:
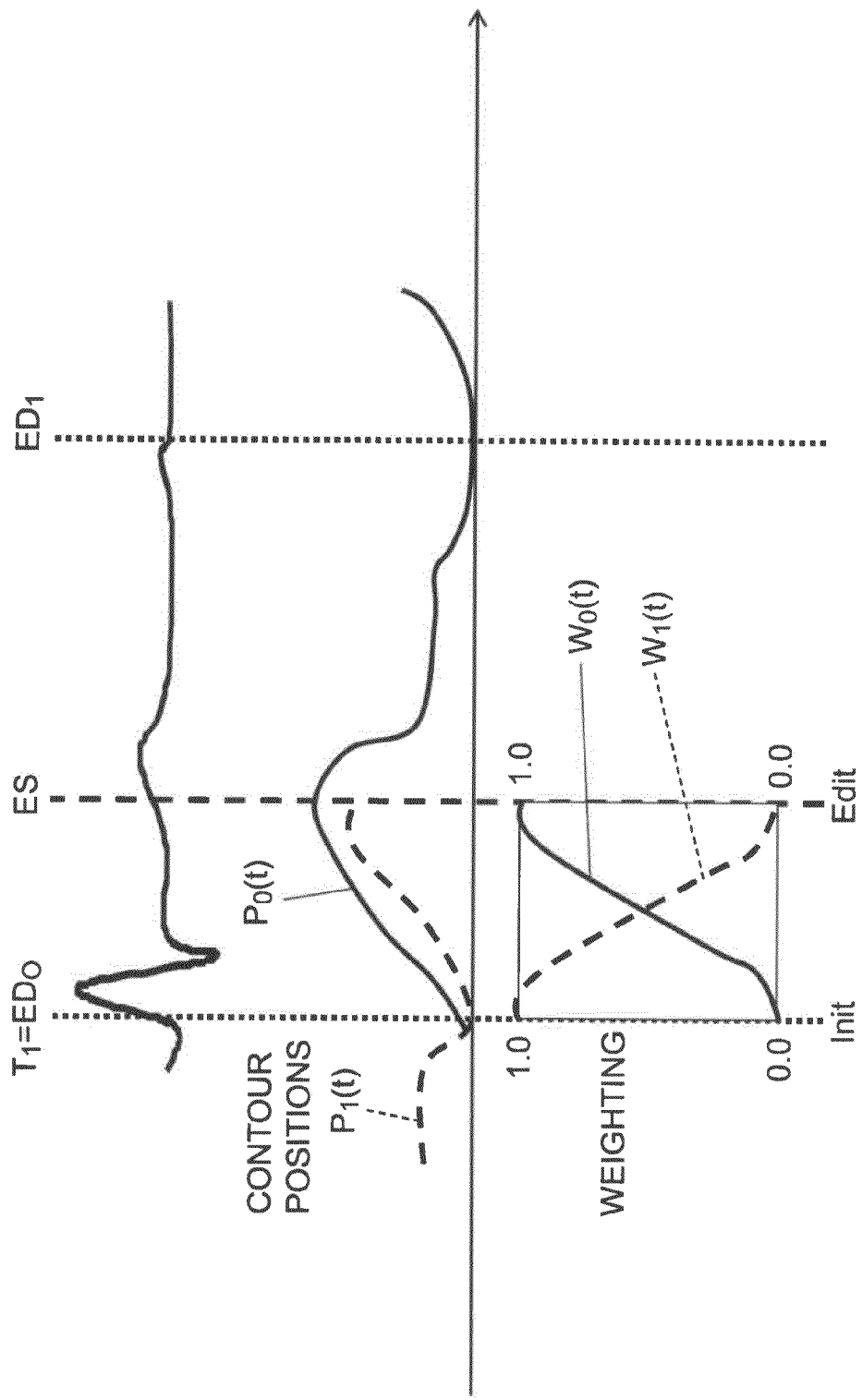
FIG. 7 is an explanatory diagram of a weighting process related to an illustrative embodiment of this invention.

Here, a specific example of the second method will be described with reference to FIG. 7. For example, for the contour position $P_0(t)$, the first weighting function $W_0(t)$ is applied. The first weighting function $W_0(t)$ is a weighting function in which the weighting becomes "0" in the end diastole $ED_0$ and gradually increases as time progresses from the end diastole $ED_0$ to the end systole ES to become "1" in the end systole ES.

Moreover, for the contour position $P_1(t)$, the second weighting function $W_1(t)$ is applied. The second weighting function $W_1(t)$ is a weighting function in which the weighting becomes in the end diastole $ED_0$ and gradually decreases as time progresses from the end diastole $ED_0$ to the end systole ES to become "0" in the end systole ES.

The position correction section 14 applies the first weighting function $W_0(t)$ to the contour position $P_0(t)$ and applies the second weighting function $W_1(t)$ to the contour position $P_1(t)$. Then, the position correction section 14 obtains the contour position P(t) in each cardiac phase within one heartbeat by adding the contour position $P_0(t)$ weighted by the first weighting function $W_0(t)$ and the contour position $P_1(t)$ weighted by the second weighting function $W_1(t)$.

A specific example of the third illustrative embodiment will be described with reference to FIGS. 8-11. As will be described in the third illustrative embodiment, a cross section (hereinafter also referred to as "short-axis cross section") along the short axis of a heart is scanned by the ultrasonic probe 2 and the transmission/reception section 3 to acquire and display cross-sectional image data (hereinafter referred to as "short-axis image data") in the short-axis cross section. First, the processes from step S30 to step S33 described above are implemented.

Figure 8:
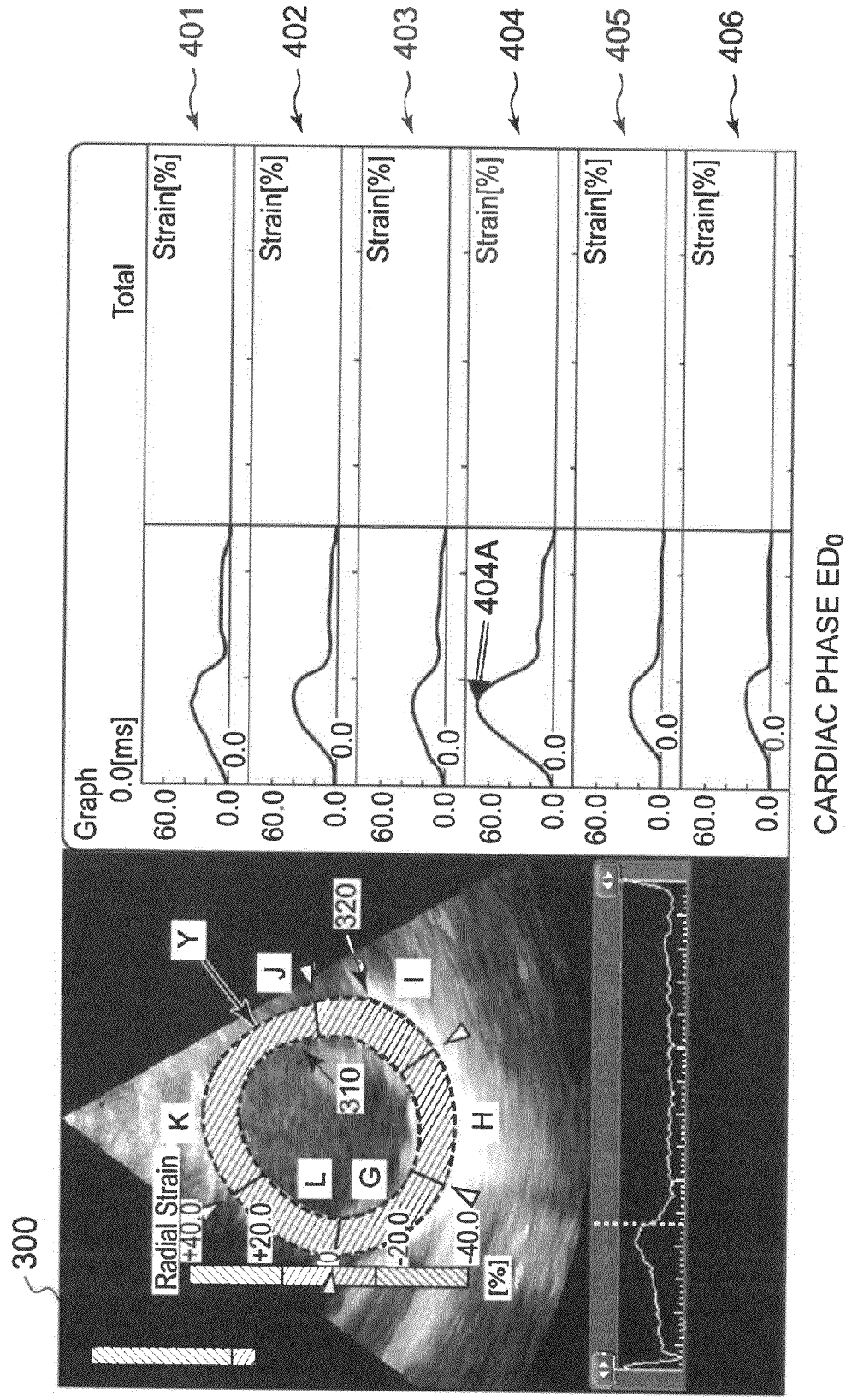
FIG. 8 is a diagram showing an image acquired by an ultrasonic imaging apparatus related to a third illustrative embodiment of this invention as well as wall-motion information.

FIG. 8 shows the results of the processes up to step S33. As an example, the display controller 7 causes the display 81 to display a short-axis image 300 and also superimposes an endocardium marker 310 and an epicardium marker 320 on the short-axis image 300 and causes the display 81 to display the same. The short-axis image 300 shown in FIG. 8 is a cross-sectional image acquired in the cardiac phase $ED_0$ (end diastole).

Moreover, the display controller 7 causes the display 81 to display the wall-motion information obtained by the motion-information calculator 20.

As an example, the display controller 7 causes the display 81 to display graphs 401-406.

Graph 401 is a graph showing changes over time in the ratio of change in wall thickness (radial strain (%)) in region G of the myocardium.

Graph 402 is a graph showing the ratio of change in wall thickness in region H.

Graph 403 is a graph showing the ratio of change in wall thickness in region I.

Graph 404 is a graph showing the ratio of change in wall thickness in region J.

Graph 405 is a graph showing the ratio of change in wall thickness in region K.

Graph 406 is a graph showing the ratio of change in wall thickness in region L.

In graphs 401-406, the horizontal axis indicates the cardiac phase while the vertical axis indicates the ratio of change in wall thickness (%) in the short axis.

In the example shown in FIG. 8, the tracking position of the epicardium has deviated in the anterior wall region (indicated by arrow Y and arrow 404A) in the cardiac phase $ED_0$ (end diastole) and the strain value in this region is overestimated.

Figure 9:
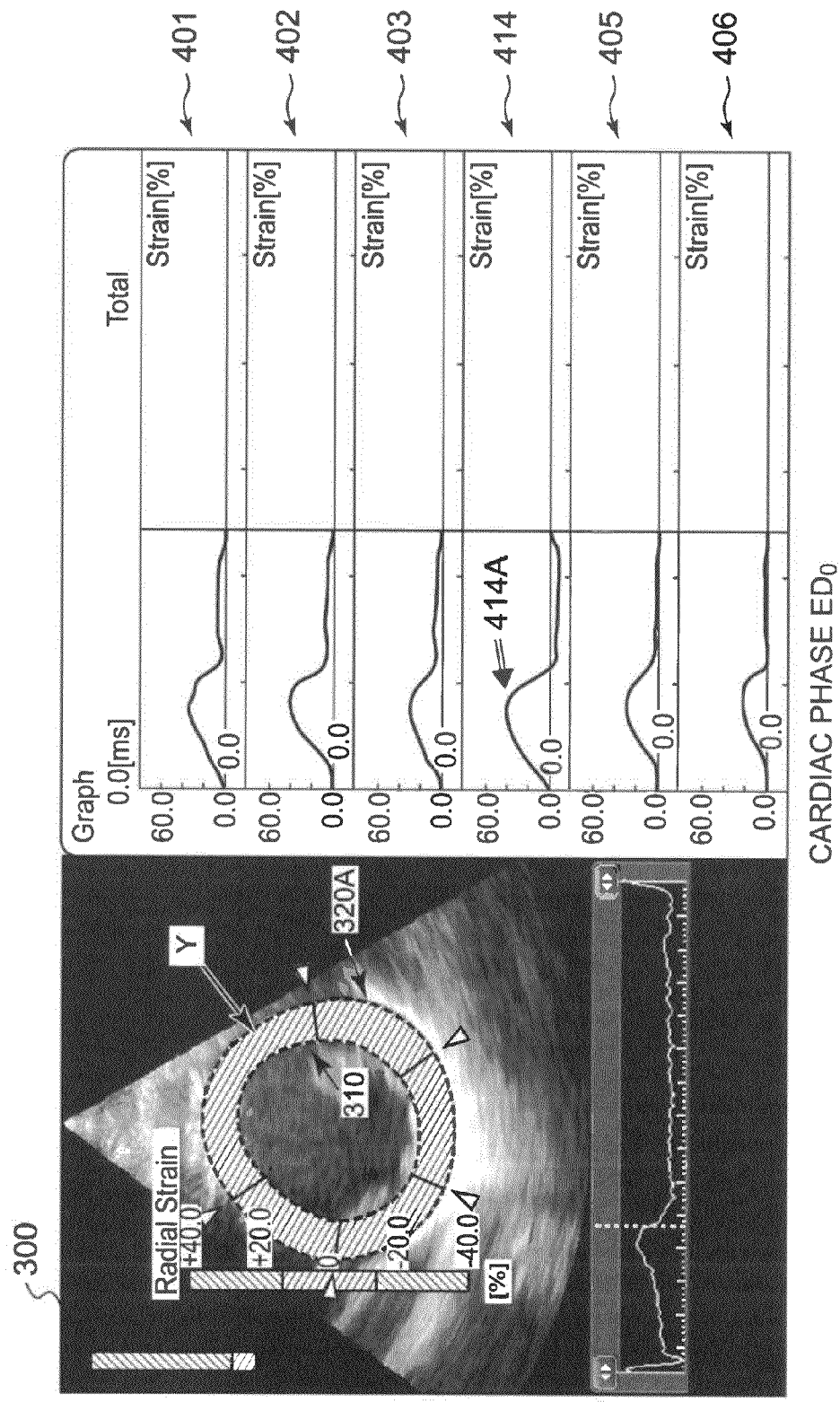
FIG. 9 is a diagram showing an image acquired by an ultrasonic imaging apparatus related to a third illustrative embodiment of this invention as well as wall-motion information.

FIG. 9 shows a state in which the contour position of the anterior wall region has been corrected in step S34. FIG. 9 shows the corrected epicardium marker 320A. Moreover, the values of graph 404 (location indicated by arrow 414A) are also corrected according to this correction operation and displayed as graph 414.

Figure 10:
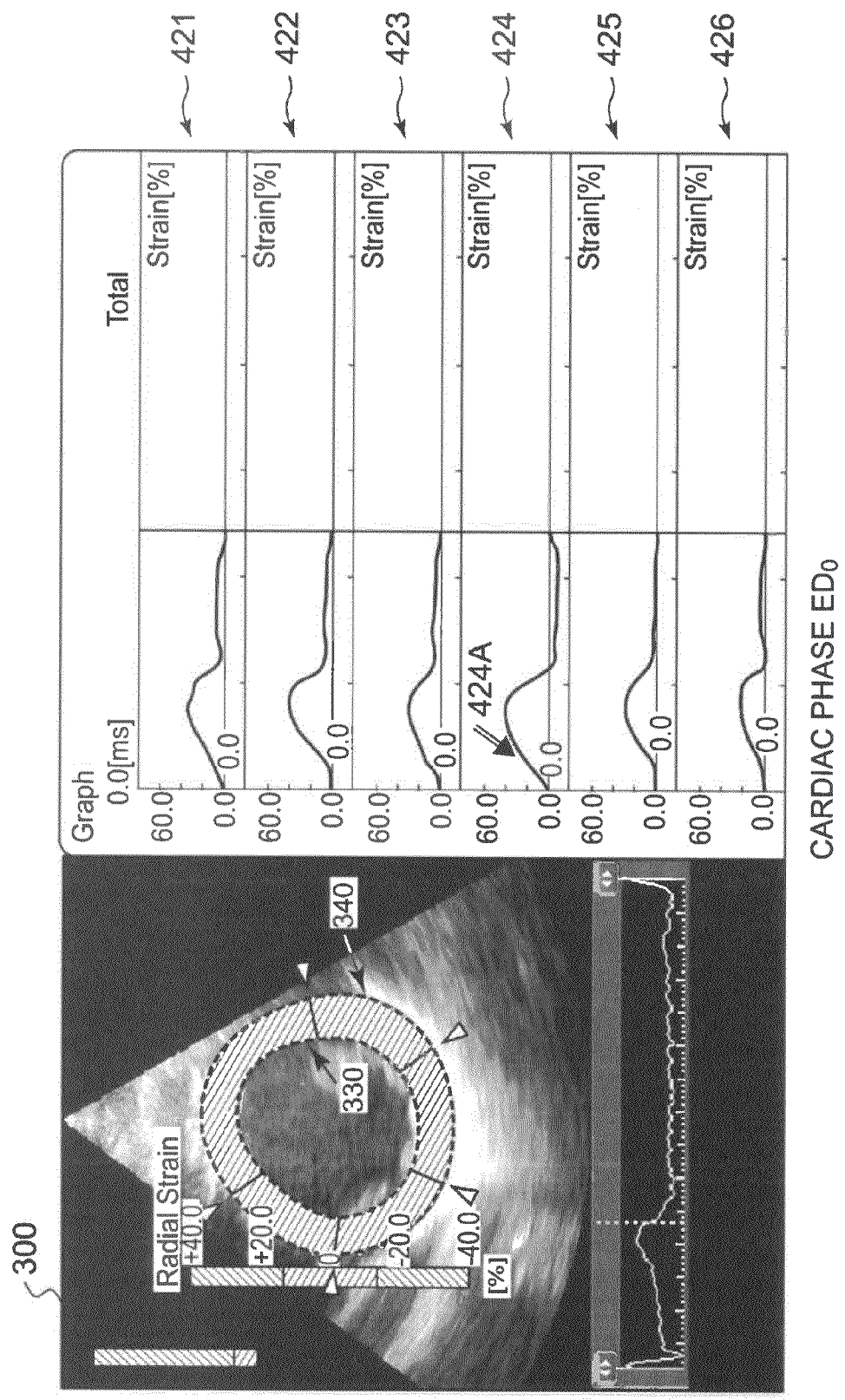
FIG. 10 is a diagram showing an image acquired by an ultrasonic imaging apparatus related to a third illustrative embodiment of this invention as well as wall-motion information.

FIG. 10 shows a state after the processes from step S35 to step S37 are executed. The anterior wall region during systole is updated and a new endocardium marker 330 and epicardium marker 340 are displayed. Furthermore, the graphs of the ratio of change in wall thickness are updated to graphs 421-426 and the ratio of change in wall thickness is represented more accurately (location indicated by arrow 424A).

Figure 11:
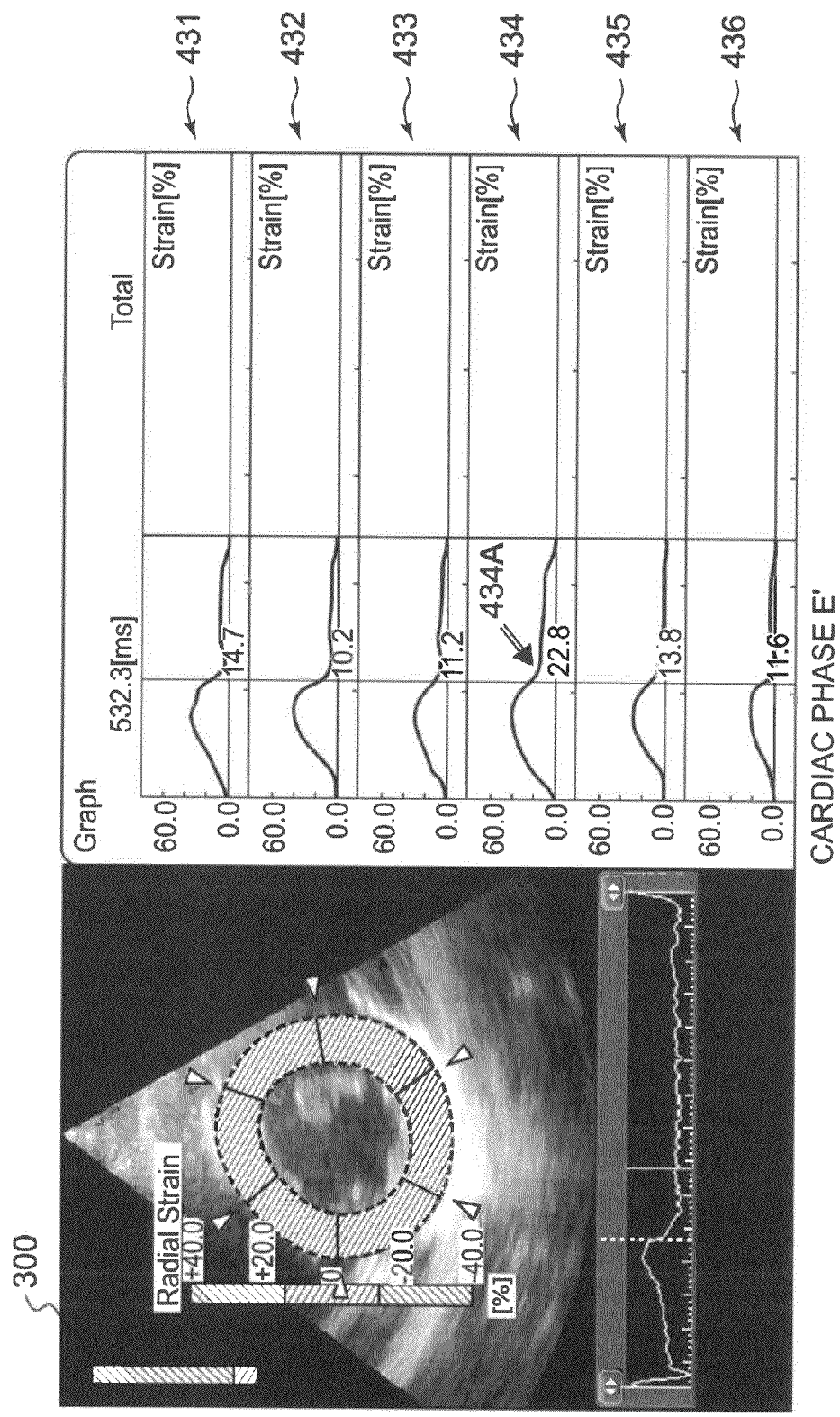
FIG. 11 is a diagram showing an image acquired by an ultrasonic imaging apparatus related to a third illustrative embodiment of this invention as well as wall-motion information.

Furthermore, in the example shown in FIG. 10, a tracking deviation has occurs after the cardiac phase E' in the tracking of the anterior wall region during diastole. For this reason, the retracking process (ReTrack2 function) performed by the third tracking section 13 is executed. FIG. 11 shows the state after the ReTrack2 function is executed. FIG. 11 shows the graphs 431-436 created after the retracking process performed by the third tracking section 13. As a result of the retracking process, the tracking deviations are resolved and the ratios of change in wall thickness are evaluated more accurately. For example, as in the location indicated by arrow 434A in graph 434, the ratio of change in wall thickness is evaluated accurately.

Modified Examples of the Second Illustrative Embodiment and the Third Illustrative Embodiment Next, modified examples of the second illustrative embodiment and the third illustrative embodiment described above will be described.

In the second illustrative embodiment described above, the ReTrack1 function is executed only for systole, but this function may also be applied to diastole. Specifically, assuming that the cyclical movements of the heart follow the same path, the contour position in the end diastole $ED_0$ may be considered equivalent to the contour position in the end diastole $ED_1$. Based on this assumption, in the second illustrative embodiment, by applying the process of step S26 to the process of step S27, the diastolic contour position $P_2(t)$ is updated.

In other words, the position correction section 14 obtains the contour position P(t) in each cardiac phase included in the period (diastole) from the end systole ES to the end diastole $ED_1$ so that it passes through the corrected contour position (second initial contour position IC2) in the end systole ES and through the contour position (first initial contour position IC1) equivalent to the position in the end diastole $ED_0$ in the end diastole $ED_1$. That is, during diastole, the contour settings or the correction results of the end systole ES and the end diastole $ED_1$ are used as restraining conditions for tracking.

Moreover, in the third illustrative embodiment described above, particularly in step S34, when the second tracking section 12 receives the correction of the contour position in the end diastole $ED_0$, under the condition that the contour position in the end diastole $ED_1$ is equivalent to the contour position in the end diastole $ED_0$, the contour position near the end diastole $ED_1$ may be preliminarily automatically corrected in conjunction with the correction of the contour position in the end diastole $ED_0$. FIG. 9 shows an example of updating the contour position near the end diastole $ED_1$ in conjunction with the correction of the contour position in the end diastole $ED_0$.

Fourth Illustrative Embodiment

Next, an ultrasonic imaging apparatus related to a fourth illustrative embodiment of this invention will be described with reference to FIG. 12. In the illustrative embodiments described above, the subject is two-dimensional moving image data representing the heart, but the subject may also be moving image data with three-dimensionally acquirable volume. In other words, based on volume data represented in three-dimensional images, the ultrasonic imaging apparatus related to the fourth illustrative embodiment tracks a three-dimensional contour of the endocardium and a three-dimensional contour of the epicardium to obtain wall-motion information. In the fourth illustrative embodiment, the application of the second illustrative embodiment to volume data representing the heart will be described as one example.

The processes related to the fourth illustrative embodiment are basically the same as the processes of step S20 to step S28 in the second illustrative embodiment, but because the subject is three-dimensional image data, it is necessary to adjust the image display method. A specific example of the processes related to the fourth illustrative embodiment will now be described.

In the fourth illustrative embodiment, by performing a volume scan using the ultrasonic probe 2 and the transmission/reception section 3, volume data is acquired in each cardiac phase. Then, the image generator 5 implements MPR processing for the volume data to generate MPR image data of an arbitrary cross section. For example, by implementing MPR processing for the volume data, the image generator 5 generates MPR image data of a plurality of different cross sections for each cross section. Then, on the MPR images, the contour position is set, judgments are made on tracking deviations of the tracking position, and the contour position is corrected.

Figure 12:
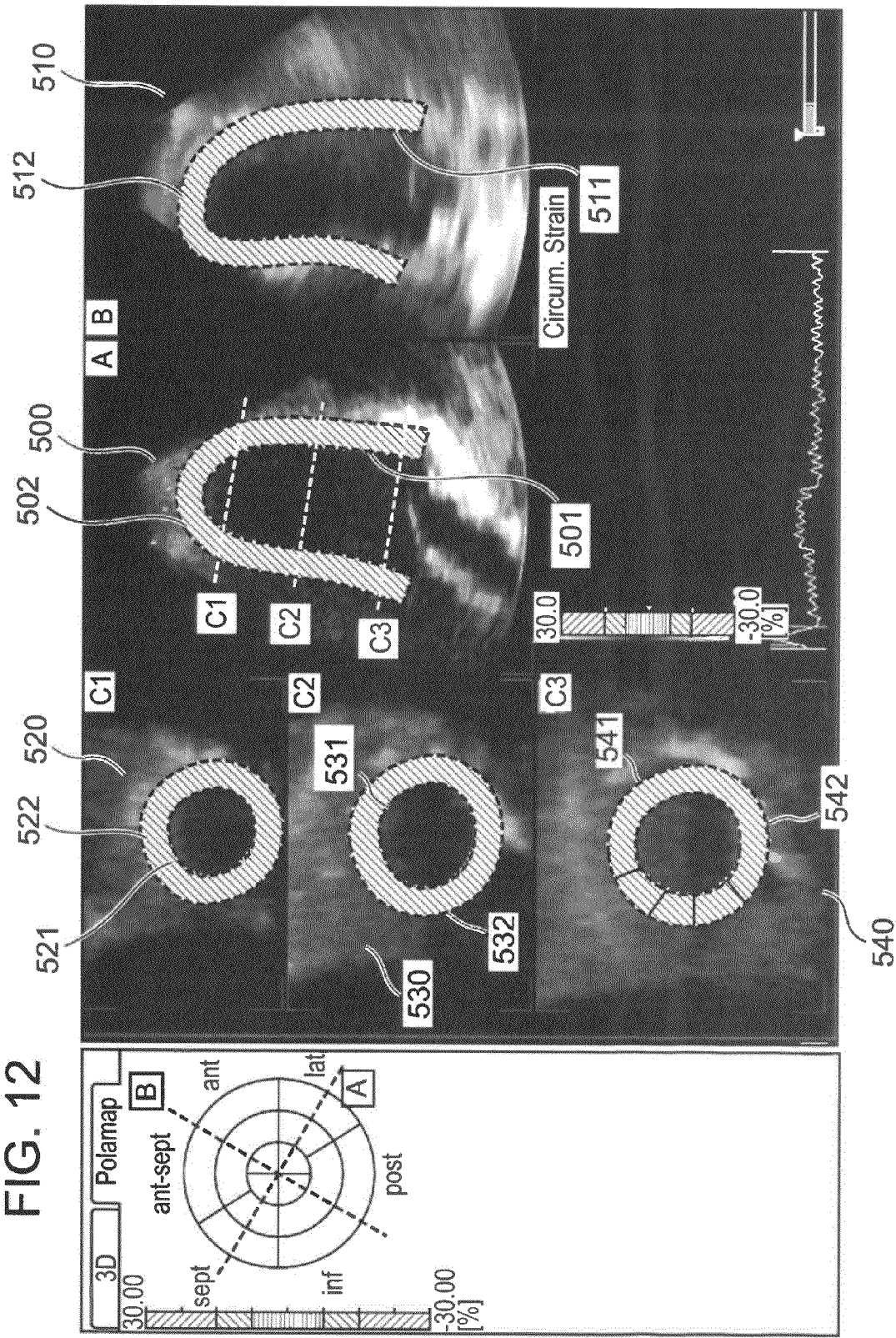
FIG. 12 is a diagram showing an image acquired by an ultrasonic imaging apparatus related to a fourth illustrative embodiment of this invention.

For example, as shown in FIG. 12, the image generator 5 generates a longitudinal image 500 (apical 4-chamber image) in a longitudinal cross section A along the longitudinal axis of the heart as well as a longitudinal image 510 in a longitudinal cross section B that is perpendicular to the longitudinal cross section A.

Furthermore, the image generator 5 generates MPR image data (short-axis image data) in a short-axis cross section (C plane) along a direction (short-axis direction) perpendicular to the longitudinal-axis direction.

For example, as shown in FIG. 12, the image generator 5 generates a short-axis image 520 in a plane C1 (apical) at a predetermined depth in the longitudinal-axis direction, generates a short-axis image 530 in a plane C2 (middle) at a predetermined depth, and generates a short-axis image 540 in a plane C3 (basal) at a predetermined depth.

The MPR image data generated by the image generator 5 is stored in the storage 6. Moreover, the position information of the plane C1, the plane C2, and the plane C3 may be preliminarily stored in the image generator 5, or the operator may specify the positions of the planes by using the operating section 82.

In step S21, the operator specifies an initial endocardial contour and an initial epicardial contour in the longitudinal image 500 and the longitudinal image 510 by referring to the longitudinal image 500 and the longitudinal image 510 displayed on the display 81 and using the operating section 82. When the initial contours are thus specified by the operator, coordinate information of the initial endocardial contour and coordinate information of the initial epicardial contour in the longitudinal cross section A are output from the user interface (UI) 8 to the image processor 10. In the same way, coordinate information of the initial endocardial contour and coordinate information of the initial epicardial contour in the longitudinal cross section B are output from the user interface (UI) 8 to the image processor 10.

Based on the coordinate information of the initial endocardial contour in the longitudinal cross section A and the coordinate information of the initial endocardial contour in the longitudinal cross section B, the image processor 10 spatially interpolates an endocardial contour in the circumferential direction to obtain the position of a three-dimensional initial contour of the endocardium. In the same way, based on the coordinate information of the initial epicardial contour in the longitudinal cross section A and the coordinate information of the initial epicardial contour in the longitudinal cross section B, the image processor 10 spatially interpolates an epicardial contour in the circumferential direction to obtain the position of a three-dimensional initial contour of the epicardium.

Then, in step S22, the first tracking section 11 defines the three-dimensional initial contour of the endocardium as the tracking subject. By using the ST method to perform pattern matching of the volume data acquired in each cardiac phase, the first tracking section 11 obtains the position of each point composing the three-dimensional contour of the endocardium in each cardiac phase.

In the same way, the first tracking section 11 defines the three-dimensional initial contour of the epicardium as the tracking subject. Using the ST method, the first tracking section 11 obtains the position of each point composing the three-dimensional contour of the epicardium in each cardiac phase. In this way, the first tracking section 11 tracks the three-dimensional contour of the endocardium and the three-dimensional contour of the epicardium. FIG. 12 shows the tracking results after the processes of step S22.

Based on the three-dimensional contour position of the endocardium and the three-dimensional contour position of the epicardium in each cardiac phase, the motion-information calculator 20 obtains the wall-motion information in the longitudinal cross section A, the wall-motion information in the longitudinal cross section B, the wall-motion information in the plane C1, the wall-motion information in the plane C2, and the wall-motion information in the plane C3.

Moreover, the marker generator 71 generates an endocardium marker representing the endocardium and an epicardium marker representing the epicardium in each of the longitudinal cross section A, the longitudinal cross section B, the plane C1, the plane C2, and the plane C3. Then, the display controller 7 causes the display 81 to display the MPR images, endocardium markers, epicardium markers, and wall-motion information of each cardiac phase.

For example, as shown in FIG. 12, the display controller 7 causes the display 81 to display, for each cardiac phase, the longitudinal image 500, the longitudinal image 510, the short-axis image 520, the short-axis image 530, and the short-axis image 540 of each cardiac phase.

Furthermore, the display controller 7 superimposes an endocardium marker 501 and an epicardium marker 502 of each cardiac phase on the longitudinal image 500 and causes the display 81 to display the same.

In the same way, the display controller 7 superimposes an endocardium marker 511 and an epicardium marker 512 of each cardiac phase on the longitudinal image 510 and causes the display 81 to display the same.

Moreover, the display controller 7 superimposes an endocardium marker 521 and an epicardium marker 522 of each cardiac phase on the short-axis image 520 and causes the display 81 to display the same.

Moreover, the display controller 7 superimposes an endocardium marker 531 and an epicardium marker 532 of each cardiac phase on the short-axis image 530 and causes the display 81 to display the same.

Moreover, the display controller 7 superimposes an endocardium marker 541 and an epicardium marker 542 of each cardiac phase on the short-axis image 540 and causes the display 81 to display the same.

Furthermore, the display controller 7 assigns colors corresponding to the degree of the wall-motion information obtained by the motion-information calculator 20 to the region between the endocardium and the epicardium, superimposes the colors on each MPR image, and causes the display 81 to display the same.

By comparing the endocardial and epicardial contour positions represented in the MPR image displayed on the display 81 with the contour positions acquired through ST processing, the operator makes judgments regarding tracking deviations. When a tracking deviation is observed, in step S24, the operator corrects the location at which the tracking deviation has occurred on the MPR image. Then, the processes of step S25 to step S27 are executed for the three-dimensional contour position.

The first illustrative embodiment, third illustrative embodiment, and modified examples thereof described above may be applied to the fourth illustrative embodiment.

Moreover, in the first to fourth illustrative embodiments described above, the subject is not limited to the heart and may also be arterial vessels such as the carotid arteries that repeat expansion and contraction in synchronization with the cardiac cycle.

The user interface (UI) 8 comprises the display 81 and the operating section 82. The display 81 may be composed of a monitor, such as a CRT monitor or a liquid crystal display, to display cross-sectional images and three-dimensional images on the screen.

The operating section 82 may be composed of a keyboard, mouse, trackball, TCS (Touch Command Screen), or the like, to issue various instructions through operations by the operator.

The controller 9 is connected to each section of the ultrasonic imaging apparatus 1 and controls the operation of each section. The user interface (UI) 8 and the controller 9 together constitute one example of a "ROI setting part". "first-ROI-setting part", and "second-ROI setting part" of this invention.

Moreover, the image generator 5, the display controller 7, the controller 9, the image processor 10, and the motion-information calculator 20 comprise a CPU (Central Processing Unit) and memory devices that are not shown in the diagrams, such as ROM (Read Only Memory), RAM (Random Access Memory), and the like (not shown).

The memory devices store an image generation program for executing functions of the image generator 5, a display control program for executing the functions of the display controller 7, a control program for executing the functions of the controller 9, an image processing program for executing the functions of the image processor 10, and a motion-information calculation program for executing the functions of the motion-information calculator 20.

Moreover, the display control program includes a marker generation program for executing the functions of the marker generator 71 and a color assignment program for executing the functions of the color assignment section 72.

Moreover, the image processing program includes a first tracking program for executing the functions of the first tracking section 11, a second tracking program for executing the functions of the second tracking section 12, a third tracking program for executing the functions of the third tracking section 13, and a position correction program for executing the functions of the position correction section 14. By executing each program, the CPU executes the functions of each section.

(MRI Device)

An ultrasonic imaging apparatus has been described as an example of the medical imaging apparatus, but as another example of the medical imaging apparatus, an MRI device may be used. The MRI device collects magnetic resonance signals from a subject by, for example, arranging the subject in a magnetostatic field and applying a gradient magnetic field and a high-frequency magnetic field to the subject. Then, based on the collected magnetic resonance signals, the MRI device generates MR image data representing the subject.

By capturing the heart of the subject using this MRI device, MR image data representing the heart is acquired. Then, by executing the processes related to the first to fourth illustrative embodiments using the image processor 10 and the motion-information calculator 20 as described above, it is possible to correct tracking deviations of a contour during systole and more accurately provide motion information of a tissue. The MR image data constitutes one example of the "medical image data" of this invention.

(X-Ray CT Device)

Moreover, as another example of the medical imaging apparatus, an X-ray CT device may be used. The X-ray CT device generates CT image data representing a subject by rotating an X-ray tube and an X-ray detected arranged with the subject in between around the subject to capture images.

By capturing the heart of the subject using this X-ray CT device, CT image data representing the heart is acquired. Then, by executing the processes related to the first to fourth illustrative embodiments using the image processor 10 and the motion-information calculator 20 as described above, it is possible to correct tracking deviations of a contour during systole and more accurately provide motion information of a tissue. The CT image data constitutes one example of the "medical image data" of this invention.

(Medical Image Processing Apparatus)

Moreover, the medical image processing apparatus may be composed by the storage 6, the display controller 7, the user interface (UI) 8, the controller 9, the image processor 10, and the motion-information calculator 20 described above. When the processes related to the first to fourth illustrative embodiments described above are executed using this medical image processing apparatus, as in the medical imaging apparatus described above, it is possible to correct tracking deviations of a contour during systole and more accurately provide motion information of a tissue.

The medical image processing apparatus may execute processes for any medical image data. e.g. the ultrasonic image data acquired by the ultrasonic imaging apparatus 1, the MR image data acquired by the MRI device, and the CT image data acquired by the X-ray CT device.

What is claimed is:

1. A medical imaging apparatus comprising:
an imaging part configured to capture a cyclically moving subject in order to acquire a plurality of medical image data representing said subject over a single cycle or more;
a ROI setting part configured to set a first region of interest of a tissue represented in medical image data acquired in a first time phase included in a one-cycle interval and to set a second region of interest of said tissue represented in medical image data acquired in a second time phase differing from said first time phase included in said one-cycle interval;
a tracking part configured to track in each time phase a position corresponding to said first region of interest in said one-cycle interval including remaining time phases based on medical image data acquired in each time phase included in said one-cycle interval, and configured to track in each time phase a position corresponding to said second region of interest in said one-cycle interval including the remaining time phases based on the medical image data acquired in said each time phase;
a position correction part configured to obtain position information of a region of interest of said tissue in said each time phase that passes through both the position of said first region of interest set in said first time phase and the position of said second region of interest set in said second time phase, based on position information of said first region of interest and said second region of interest in each time phase acquired by said tracking part;
a motion-information calculator configured to obtain motion information of said tissue based on said position information of the region of interest in said each time phase obtained by said position correcting part; and
a display controller configured to cause a display to display said motion information,
wherein said position correction part is configured to obtain position information of the region of interest of said tissue in each time phase by smoothly connecting the position of said first region of interest and the position of said second region of interest in a time phase between said first time phase and said second time phase.

2. The medical imaging apparatus of claim 1, wherein:
said imaging part is configured to capture a heart as said subject, in order to acquire a plurality of medical image data representing said heart over said single cycle or more; and
said ROI setting part is configured to define a time phase during end diastole of said heart as said first time phase and a time phase during end systole of said heart as said second time phase to set said first region of interest and said second region of interest.

3. The medical imaging apparatus of claim 1, wherein:
said ROI setting part is configured to set said first region of interest and said second region of interest in response to input of said first region of interest and said second region of interest from an operator.

4. The medical imaging apparatus of claim 1, wherein:
said ROI setting part is configured to detect shape information of said tissue in said first time phase and said second time phase based on brightness of said medical image data and preset shape information of said tissue to set said first region of interest and said second region of interest.

5. A medical imaging apparatus, comprising:
an imaging part configured to capture a cyclically moving subject to acquire a plurality of medical image data representing said subject over a single cycle or more;
a first-ROI setting part configured to set a first region of interest of a tissue represented by medical image data acquired in a first time phase during systole included in a one-cycle interval;
a first tracking part configured to track in each time phase a position corresponding to said first region of interest in said one-cycle interval including remaining time phases, based on medical image data acquired in each time phase included in said one-cycle interval;
a second-ROI setting part configured to correct position of said tracked first region of interest in a second time phase differing from said first time phase during systole included in said one-cycle interval after said tracking performed by said first tracking part, in order to set a second region of interest of said tissue in said second time phase;
a second tracking part configured to track in each time phase a position corresponding to said second region of interest in an interval including the interval between said first time phase and said second time phase, based on medical image data acquired in said each time phase;
a position correction part configured to obtain position information of a region of interest of said tissue in said each time phase that passes through both the position of said first region of interest in said first time phase and the position of said second region of interest in said second time phase, based on position information of said first region of interest and said second region of interest in each time phase acquired by said first tracking part and said second tracking part, respectively;
a motion-information calculator configured to obtain motion information of said tissue based on said position information of the region of interest in said each time phase obtained by said position correcting part; and
a display controller configured to cause a display to display said motion information,
wherein said position correction part is configured to obtain position information of the region of interest of said tissue in each time phase by smoothly connecting the position of said first region of interest and the position of said second region of interest in a time phase between said first time phase and said second time phase.

6. The medical imaging apparatus of claim 5, wherein:
a combination of said first time phase and said second time phase is a combination of a time phase of the end diastole and a time phase of the end systole of a heart.

7. The medical imaging apparatus of claim 5, wherein:
said first time phase is a time phase of the end diastole of a heart and said second time phase is a time phase of the end systole of said heart;
said position correction part is configured to obtain position information of a region of interest of said tissue in each time phase included in a first interval that passes through the position of said first region of interest in the time phase of said end diastole and the position of said second region of interest in the time phase of said end systole for said first interval between the time phase for said end diastole and the time phase for said end systole;
said position correction part is configured to obtain position information of the region of interest of said tissue in each time phase included in said one-cycle interval, based on position information of said second region of interest in each time phase included in a second interval between said end systole and the end time of said one-cycle interval and position information of a region of interest of said tissue in each time phase included in said obtained first interval; and
said motion-information calculator is configured to obtain motion information of said tissue based on said position information of the region of interest obtained by said position correcting part in said each time phase included in said one-cycle interval.

8. The medical imaging apparatus of claim 5, wherein:
said first time phase is a time phase of the end systole of a heart and said second time phase is a time phase of the end diastole of said heart;
said position correction part is configured to obtain position information of a region of interest of said tissue in each time phase included in a first interval that passes through the position of said first region of interest in the time phase of said end systole and the position of said second region of interest in the time phase of said end diastole for said first interval between the time phase for said end systole and the time phase for said end diastole;
said position correction part is configured to obtain position information of the region of interest of said tissue in each time phase included in said one-cycle interval, based on position information of said first region of interest in each time phase included in a second interval between said end systole and the end time of said one-cycle interval and position information of a region of interest of said tissue in each time phase included in said obtained first interval; and
said motion-information calculator is configured to obtain motion information of said tissue based on position information of the region of interest in said each time phase included in said one-cycle interval obtained by said position correction part.

9. The medical imaging apparatus of claim 1, wherein:
said position correction part is configured to obtain position information of said region of interest in said each time phase by assigning weighting according to a time to the positions of said first region of interest and said second region of interest in said each time phase and adding the positions in an interval between said first time phase and said second time phase.

10. The medical imaging apparatus of claim 1, wherein:
said imaging part is configured to acquire a plurality of three-dimensional image data as said medical image data over said single cycle or more; and
said position correction part is configured to obtain three-dimensional position information as the position information of the region of interest of said tissue in said each time phase, based on the position information of said first region of interest in said each time phase and the position information of said second region of interest in said each time phase.

11. The medical imaging apparatus of claim 1, wherein:
said imaging part is configured to acquire ultrasonic image data representing said subject as said medical image data by ultrasonically scanning said subject.

12. The medical imaging apparatus of claim 1, wherein:
said imaging part is configured to acquire MR image data representing said subject as said medical image data by applying a high-frequency magnetic field and a gradient magnetic field to said subject disposed in a magnetostatic field and collecting magnetic resonance signals.

13. A medical image processing apparatus, comprising:
a storage configured to store a plurality of medical image data that represents a cyclically moving subject acquired by capturing the subject over a single cycle or more;
a ROI setting part configured to set a first region of interest of a tissue represented in medical image data acquired in a first time phase included in a one-cycle interval, and to set a second region of interest of said tissue represented in medical image data acquired in a second time phase differing from said first time phase included in said one-cycle interval;
a tracking part configured to track in each time phase a position corresponding to said first region of interest in said one-cycle interval including remaining time phases, based on medical image data acquired in each time phase included in said one-cycle interval and configured to track in each time phase a position corresponding to said second region of interest in said one-cycle interval including the remaining time phases, based on the medical image data acquired in said each time phase;
a position correction part configured to obtain position information of a region of interest of said tissue in said each time phase that passes through the position of said first region of interest set in said first time phase and the position of said second region of interest set in said second time phase, based on position information of said first region of interest and said second region of interest in each time phase acquired by said tracking part;
a motion-information calculator configured to obtain motion information of said tissue based on said position information of the region of interest in said each time phase obtained by said position correcting part; and
a display controller configured to cause a display to display said motion information,
wherein said position correction part is configured to obtain position information of the region of interest of said tissue in each time phase by smoothly connecting the position of said first region of interest and the position of said second region of interest in a time phase between said first time phase and said second time phase.

14. A medical image processing apparatus, comprising:
a storage configured to store a plurality of medical image data that represents a cyclically moving subject acquired by capturing the subject over a single cycle or more;
a first-ROI setting part configured to set a first region of interest of a tissue represented by medical image data acquired in a first time phase during systole included in a one-cycle interval;
a first tracking part configured to track in each time phase a position corresponding to said first region of interest in said one-cycle interval including remaining time phases, based on medical image data acquired in each time phase included in said one-cycle interval;
a second-ROI setting part configured to correct the position of said tracked first region of interest in a second time phase differing from said first time phase during systole included in said one-cycle interval after said tracking performed by said first tracking part, to set a second region of interest of said tissue in said second time phase;
a second tracking part configured to track in each time phase a position corresponding to said second region of interest in an interval including the interval between said first time phase and said second time phase, based on medical image data acquired in said each time phase;
a position correction part configured to obtain position information of a region of interest of said tissue in said each time phase that passes through both the position of said first region of interest in said first time phase and the position of said second region of interest in said second time phase, based on position information of said first region of interest and said second region of interest in each time phase acquired by said first tracking part and said second tracking part, respectively;
a motion-information calculator configured to obtain motion information of said tissue based on said position information of the region of interest in said each time phase obtained by said position correcting part; and
a display controller configured to cause a display to display said motion information
wherein said position correction part is configured to obtain position information of the region of interest of said tissue in each time phase by smoothly connecting the position of said first region of interest and the position of said second region of interest in a time phase between said first time phase and said second time phase.

15. An ultrasonic imaging apparatus, comprising:
an imaging part configured to capture a heart of a subject by means of ultrasound in order to acquire a plurality of ultrasonic image data representing said heart over a single cycle or more;
a ROI setting part configured to set a first region of interest of a tissue represented in ultrasonic image data acquired in a first time phase included in a one-cycle interval, and to set a second region of interest of said tissue represented in ultrasonic image data acquired in a second time phase differing from said first time phase included in said one-cycle interval;
a tracking part configured to track in each time phase a position corresponding to said first region of interest in said one-cycle interval including remaining time phases based on ultrasonic image data acquired in each time phase included in said one-cycle interval, and configured to track in each time phase a position corresponding to said second region of interest in said one-cycle interval including the remaining time phases based on the ultrasonic image data acquired in said each time phase;
a position correction part configured to obtain position information of a region of interest of said tissue in said each time phase that passes through both the position of said first region of interest set in said first time phase and the position of said second region of interest set in said second time phase, based on position information of said first region of interest and said second region of interest in each time phase acquired by said tracking part;
a motion-information calculator configured to obtain motion information of said tissue based on said position information of the region of interest in said each time phase obtained by said position correcting part; and
a display controller configured to cause a display to display said motion information,
wherein said position correction part is configured to obtain position information of the region of interest of said tissue in each time phase by smoothly connecting the position of said first region of interest and the position of said second region of interest in a time phase between said first time phase and said second time phase.

16. An ultrasonic imaging apparatus, comprising:
an imaging part configured to capture a heart of a subject by means of ultrasound to acquire a plurality of ultrasonic image data representing said heart over a single cycle or more;
a first-ROI setting part configured to set a first region of interest of a tissue represented by ultrasonic image data acquired in a first time phase during systole included in a one-cycle interval;
a first tracking part configured to track in each time phase a position corresponding to said first region of interest in said one-cycle interval including remaining time phases, based on ultrasonic image data acquired in each time phase included in said one-cycle interval;
a second-ROI setting part configured to correct the position of said tracked first region of interest in a second time phase differing from said first time phase during systole included in said one-cycle interval after said tracking performed by said first tracking part, in order to set a second region of interest of said tissue in said second time phase;
a second tracking part configured to track in each time phase a position corresponding to said second region of interest in an interval including the interval between said first time phase and said second time phase, based on ultrasonic image data acquired in said each time phase;
a position correction part configured to obtain position information of a region of interest of said tissue in said each time phase that passes through both the position of said first region of interest in said first time phase and the position of said second region of interest in said second time phase, based on position information of said first region of interest and said second region of interest in each time phase acquired by said first tracking part and said second tracking part, respectively;
a motion-information calculator configured to obtain motion information of said tissue based on said position information of the region of interest in said each time phase obtained by said position correcting part; and
a display controller configured to cause a display to display said motion information,
wherein said position correction part is configured to obtain position information of the region of interest of said tissue in each time phase by smoothly connecting the position of said first region of interest and the position of said second region of interest in a time phase between said first time phase and said second time phase.

17. An ultrasonic image processing apparatus, comprising:
a storage configured to store a plurality of ultrasonic image data that represents a heart of a subject acquired over a single cycle or more by capturing the subject by means of ultrasound;
a ROI setting part configured to set a first region of interest of a tissue represented in ultrasonic image data acquired in a first time phase included in a one-cycle interval, and to set a second region of interest of said tissue represented in ultrasonic image data acquired in a second time phase differing from said first time phase included in said one-cycle interval;
a tracking part configured to track in each time phase a position corresponding to said first region of interest in said one-cycle interval including remaining time phases, based on ultrasonic image data acquired in each time phase included in said one-cycle interval and configured to track in each time phase a position corresponding to said second region of interest in said one-cycle interval including the remaining time phases, based on the ultrasonic image data acquired in said each time phase;
a position correction part configured to obtain position information of a region of interest of said tissue in said each time phase that passes through the position of said first region of interest set in said first time phase and the position of said second region of interest set in said second time phase, based on position information of said first region of interest and said second region of interest in each time phase acquired by said tracking part;
a motion-information calculator configured to obtain motion information of said tissue based on said position information of the region of interest in said each time phase obtained by said position correcting part; and
a display controller configured to cause a display to display said motion information,
wherein said position correction part is configured to obtain position information of the region of interest of said tissue in each time phase by smoothly connecting the position of said first region of interest and the position of said second region of interest in a time phase between said first time phase and said second time phase.

18. An ultrasonic image processing apparatus, comprising:
a storage configured to store a plurality of ultrasonic image data that represents a heart of a subject acquired over a single cycle or more by capturing the subject by means of ultrasound;
a first-ROI setting part configured to set a first region of interest of a tissue represented by ultrasonic image data acquired in a first time phase during systole included in a one-cycle interval;
a first tracking part configured to track in each time phase a position corresponding to said first region of interest in said one-cycle interval including remaining time phases, based on ultrasonic image data acquired in each time phase included in said one-cycle interval;
a second-ROI setting part configured to correct the position of said tracked first region of interest in a second time phase differing from said first time phase during systole included in said one-cycle interval after said tracking performed by said first tracking part, to set a second region of interest of said tissue in said second time phase;
a second tracking part configured to track in each time phase a position corresponding to said second region of interest in an interval including the interval between said first time phase and said second time phase, based on ultrasonic image data acquired in said each time phase;
a position correction part configured to obtain position information of a region of interest of said tissue in said each time phase that passes through both the position of said first region of interest in said first time phase and the position of said second region of interest in said second time phase, based on position information of said first region of interest and said second region of interest in each time phase acquired by said first tracking part and said second tracking part, respectively;
a motion-information calculator configured to obtain motion information of said tissue based on said position information of the region of interest in said each time phase obtained by said position correcting part; and
a display controller configured to cause a display to display said motion information, wherein said position correction part is configured to obtain position information of the region of interest of said tissue in each time phase by smoothly connecting the position of said first region of interest and the position of said second region of interest in a time phase between said first time phase and said second time phase.

19. A method of processing medical images implemented by a processor programmed as a medical imaging apparatus, the method comprising:
    capturing a cyclically moving subject to acquire a plurality of medical image data representing said subject over a single cycle or more;
    setting, by the medical imaging apparatus, a first region of interest of a tissue represented in medical image data acquired in a first time phase included in a one-cycle interval, and setting a second region of interest of said tissue represented in medical image data acquired in a second time phase differing from said first time phase included in said one-cycle interval;
    tracking in each time phase a position corresponding to said first region of interest in said one-cycle interval including remaining time phases, based on medical image data acquired in each time phase included in said one-cycle interval, and tracking in each time phase a position corresponding to said second region of interest in said one-cycle interval including the remaining time phases, based on medical image data acquired in said each time phase;
    obtaining position information of a region of interest of said tissue in said each time phase that passes through both the position of said first region of interest set in said first time phase and the position of said second region of interest set in said second time phase, based on position information of said first region of interest and said second region of interest in each time phase acquired in the tracking step;
    obtaining motion information of said tissue based on said obtained position information of the region of interest in said each time phase; and
    displaying said motion information,
    wherein the obtaining step includes obtaining position information of the region of interest of said tissue in each time phase by smoothly connecting the position of said first region of interest and the position of said second region of interest in a time phase between said first time phase and said second time phase.

20. The method of processing medical images of claim 19, wherein:
    a heart is captured as said subject to acquire a plurality of medical image data representing said heart over said single cycle or more; and
    said first region of interest and said second region of interest are set by defining a time phase during end diastole of said heart as said first time phase and defining a time phase during end systole of said heart as said second time phase.

21. The method of processing medical images of claim 19, wherein:
    said first region of interest and said second region of interest are set in response to input of said first region of interest and said second region of interest from an operator.

22. The method of processing medical images of claim 19, wherein:
    said first region of interest and said second region of interest are set by detecting shape information of said tissue in said first time phase and said second time phase based on brightness of said medical image data and preset shape information of said tissue.

23. A method of processing medical images implemented by a processor programmed as a medical imaging apparatus, the method comprising:
    capturing a cyclically moving subject to acquire a plurality of medical image data representing said subject over a single cycle or more;
    setting, by the medical imaging apparatus, a first region of interest of a tissue represented by medical image data acquired in a first time phase during systole included in a one-cycle interval;
    tracking in each time phase a position corresponding to said first region of interest in said one-cycle interval including remaining time phases, based on medical image data acquired in each time phase included in said one-cycle interval;
    correcting the position of said tracked first region of interest in a second time phase differing from said first time phase during systole included in said one-cycle interval after said tracking, to set a second region of interest of said tissue in said second time phase;
    tracking in each time phase a position corresponding to said second region of interest in an interval including the interval between said first time phase and said second time phase, based on medical image data acquired in said each time phase;
    obtaining position information of a region of interest of said tissue in said each time phase that passes through both the position of said first region of interest in said first time phase and the position of said second region of interest in said second time phase, based on position information of said first region of interest and said second region of interest in said each time phase acquired in the respectively tracking steps;
    obtaining motion information of said tissue based on said obtained position information of the region of interest in said each time phase; and
    displaying said motion information,
    wherein the obtaining step includes obtaining position information of the region of interest of said tissue in said each time phase by smoothly connecting the position of said first region of interest and the position of said second region of interest in a time phase between said first time phase and said second time phase.

* * * * *